(12) United States Patent
Fontanel et al.

(10) Patent No.: US 10,795,435 B2
(45) Date of Patent: Oct. 6, 2020

(54) SYSTEM AND METHOD FOR HYBRID EYE TRACKER

(71) Applicant: Samsung Electronics Co., Ltd, Suwon-si, Gyeonggi-do (KR)

(72) Inventors: Fannie Fontanel, Sunnyvale, CA (US); Sajid Sadi, San Jose, CA (US)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 16/216,849

(22) Filed: Dec. 11, 2018

(65) Prior Publication Data

US 2020/0026349 A1    Jan. 23, 2020

Related U.S. Application Data

(60) Provisional application No. 62/700,748, filed on Jul. 19, 2018.

(51) Int. Cl.
   *G06F 3/01*     (2006.01)
   *A61B 3/113*    (2006.01)
   *G06F 3/0484*   (2013.01)

(52) U.S. Cl.
   CPC .............. *G06F 3/013* (2013.01); *A61B 3/113* (2013.01); *G06F 3/0484* (2013.01)

(58) Field of Classification Search
   CPC ......... G06F 3/013; G06F 3/0484; A61B 3/113
   See application file for complete search history.

(56) References Cited

U.S. PATENT DOCUMENTS

| | | | |
|---|---|---|---|
| 5,410,376 | A  | 4/1995  | Cornsweet et al. |
| 9,001,220 | B2 | 4/2015  | Kim et al. |
| 9,898,082 | B1 | 2/2018  | Greenwald |
| 2001/0030644 | A1 | 10/2001 | Allport |
| 2008/0130950 | A1 | 6/2008  | Miklos et al. |

(Continued)

FOREIGN PATENT DOCUMENTS

| | | |
|---|---|---|
| CN | 108171728 A | 6/2018 |
| KR | 10-2010-0125484 A | 12/2010 |

(Continued)

OTHER PUBLICATIONS

Lee, et al., "Live Demonstration: Gesture-Based remote control using stereo pair of dynamic vision sensors", 2012 IEEE International Symposium on Circuits and Systems, May 2012, 5 pages.

(Continued)

*Primary Examiner* — Peter D McLoone

(57) ABSTRACT

A system and method enable an electronic device to perform gaze tracking operations. The electronic device includes one or more cameras and at least one processor. The one or more cameras include a Dynamic Vision Sensor (DVS) camera. The one or more cameras are configured to capture features of an eye of a wearer of the electronic device The processor is configured to receive, from the one or more cameras, an image or pixel stream associated with the eye, determine an initial pose of the eye based on the image or pixel stream, receive DVS pixel data from the DVS camera, track one or more changes to the initial pose of the eye based on the DVS pixel data, and based on the one or more changes to the initial pose of the eye, determine a gaze of the wearer.

20 Claims, 11 Drawing Sheets

(56) References Cited

U.S. PATENT DOCUMENTS

| | | | |
|---|---|---|---|
| 2011/0113441 | A1 | 5/2011 | Jeong et al. |
| 2014/0002349 | A1 | 1/2014 | Hansen |
| 2014/0197922 | A1 | 7/2014 | Stanwood et al. |
| 2014/0334666 | A1 | 11/2014 | Lankford et al. |
| 2016/0085302 | A1 | 3/2016 | Publicover et al. |
| 2017/0213105 | A1 | 7/2017 | Ji et al. |
| 2017/0286771 | A1 | 10/2017 | Ishii et al. |
| 2018/0122333 | A1* | 5/2018 | Horiike .................... G06F 3/01 |
| 2018/0173948 | A1 | 6/2018 | Gousev et al. |
| 2018/0295337 | A1* | 10/2018 | Hicks ..................... G06F 3/017 |

FOREIGN PATENT DOCUMENTS

| | | |
|---|---|---|
| KR | 10-2015-0049243 A | 5/2015 |
| KR | 10-1548195 B1 | 9/2015 |
| KR | 10-2017-0043880 A | 4/2017 |
| WO | 2019/067731 A1 | 4/2019 |

OTHER PUBLICATIONS

"DVS: Applications", iniLabs Ltd, Accessed Jul. 18, 2018, 5 pages. https://inilabs.com/dvs-applications/.

Delbrück, et al., "D5.5 Silicon retina and other novel approaches for eye tracking", Communication by Gaze Interaction (COGAIN), IST-2003-511598, Feb. 2008, 51 pages.

Gisler, et al., "Eye Tracking using Event-Based Silicon Retina", Institute of Neuroinformatics UNI-ETH Zürich, Winter Semester 2006/2007, 29 pages.

Notification of Transmittal of the International Search Report and the Written Opinion of the International Searching Authority, or the Declaration dated Oct. 30, 2019 in connection with International Patent Application No. PCT/KR2019/008955, 10 pages.

Lenz et al., "Event-based Face Detection and Tracking in the Blink of an Eye", Mar. 27, 2018, 9 pages.

European Search Report dated Oct. 21, 2019 in connection with European Patent Application No. 19 18 7250, 13 pages.

* cited by examiner

SYSTEM AND METHOD FOR HYBRID EYE TRACKER

CROSS-REFERENCE TO RELATED APPLICATION(S) AND CLAIM OF PRIORITY

This application claims priority under 35 U.S.C. § 119(e) to U.S. Provisional Patent Application No. 62/700,748 filed on Jul. 19, 2018 and entitled "HYBRID EYE TRACKER". The above-identified provisional patent application is hereby incorporated by reference in its entirety.

TECHNICAL FIELD

This disclosure relates generally to optical systems. More specifically, this disclosure relates to eye tracking using Dynamic Vision Sensor (DVS) cameras.

BACKGROUND

Augmented reality (AR) glasses are a growing market. Current eye tracking technology using conventional cameras and an illumination system requires the illumination system to be turned on continuously to achieve optimal dynamic range for object recognition. While eye tracking technology using conventional cameras and infrared illumination has been achieved, these conventional eye tracking approaches require a large amount of processing power, which is a strain on battery life. In turn, current AR glasses come with a high purchase price. Even though eye tracking can be achieved using a conventional camera without an illumination system to reduce cost, the dynamic range of a conventional camera makes recognition of objects in the dark difficult. Furthermore, conventional cameras require a high frame rate to be able to accurately track eye movement.

SUMMARY

This disclosure provides a system and method for eye tracking or gaze tracking, or both, such as for use with a head mounted display system.

In a first embodiment, an electronic device is provided. The electronic device includes one or more cameras and a processor. The one or more cameras include a Dynamic Vision Sensor (DVS) camera and are configured to capture pixel information such as pixel changes from or caused by an eye of a wearer of the electronic device. The processor is configured to receive, from the one or more cameras, information associated with the eye, initialize an initial pose (for example, determine, calculate, or estimate an initial pose) of the eye based on the information, receive DVS pixel data, track one or more changes to the initial pose of the eye based on the DVS pixel data, and based on the one or more changes to the initial pose of the eye, determine a gaze of the wearer.

In a second embodiment, a method is provided. The method includes capturing pixel changes from an eye of a wearer. The method also includes initializing an initial pose of the eye. The method also includes receiving DVS pixel data from the at least one DVS camera. The method further includes tracking one or more changes to the initial pose of the eye based on the DVS pixel data. The method further includes determining a gaze of the wearer based on the one or more changes to the initial pose of the eye.

In a third embodiment, a non-transitory computer readable medium configured to store a plurality of instructions is provided. The plurality of instructions, when executed by at least one processor, are configured to cause the at least one processor to receive from one or more cameras information associated with the eye; initialize an initial pose of the eye based on the information; receive Dynamic Vision Sensor (DVS) pixel data from at least one DVS camera; track one or more changes to the initial pose of the eye based on the DVS pixel data; and determine a gaze of the wearer based on the one or more changes to the initial pose of the eye.

Before undertaking the DETAILED DESCRIPTION below, it may be advantageous to set forth definitions of certain words and phrases used throughout this patent document. The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrase "associated with," as well as derivatives thereof, means to include, be included within, interconnect with, contain, be contained within, connect to or with, couple to or with, be communicable with, cooperate with, interleave, juxtapose, be proximate to, be bound to or with, have, have a property of, have a relationship to or with, or the like.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

As used herein, the terms "have," "may have," "include," "may include," "can have," or "can include" a feature (e.g., a number, function, operation, or a component such as a part) indicate the existence of the feature and do not exclude the existence of other features.

As used herein, the terms "A or B," "at least one of A and/or B," or "one or more of A and/or B" may include all possible combinations of A and B. For example, "A or B," "at least one of A and B," "at least one of A or B" may indicate all of (1) including at least one A, (2) including at least one B, or (3) including at least one A and at least one B.

As used herein, the terms "first" and "second" may modify various components regardless of importance and do not limit the components. These terms are only used to distinguish one component from another. For example, a first user device and a second user device may indicate different user devices from each other regardless of the order or importance of the devices. For example, a first component may be denoted a second component, and vice versa without departing from the scope of the present disclosure.

It will be understood that when an element (e.g., a first element) is referred to as being (operatively or communicatively) "coupled with/to," or "connected with/to" another element (e.g., a second element), it can be coupled or connected with/to the other element directly or via a third element. In contrast, it will be understood that when an element (e.g., a first element) is referred to as being "directly coupled with/to" or "directly connected with/to" another element (e.g., a second element), no other element (e.g., a third element) intervenes between the element and the other element.

As used herein, the terms "configured (or set) to" may be interchangeably used with the terms "suitable for," "having the capacity to," "designed to," "adapted to," "made to," or "capable of" depending on circumstances. The term "configured (or set) to" does not essentially mean "specifically designed in hardware to." Rather, the term "configured to" may mean that a device can perform an operation together with another device or parts.

For example, the term "processor configured (or set) to perform A, B, and C" may mean a generic-purpose processor (e.g., a CPU or application processor) that may perform the operations by executing one or more software programs stored in a memory device or a dedicated processor (e.g., an embedded processor) for performing the operations.

The terms as used herein are provided merely to describe some embodiments thereof, but not to limit the scope of other embodiments of the present disclosure. It is to be understood that the singular forms "a," "an," and "the" include plural references unless the context clearly dictates otherwise. All terms including technical and scientific terms used herein have the same meaning as commonly understood by one of ordinary skill in the art to which the embodiments of the present disclosure belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein. In some cases, the terms defined herein may be interpreted to exclude embodiments of the present disclosure.

For example, examples of the electronic device according to embodiments of the present disclosure may include at least one of a smartphone, a tablet personal computer (PC), a mobile phone, a video phone, an e-book reader, a desktop PC, a laptop computer, a netbook computer, a workstation, a PDA (personal digital assistant), a portable multimedia player (PMP), an MP3 player, a mobile medical device, a camera, or a wearable device (e.g., smart glasses, a head-mounted device (HMD), electronic clothes, an electronic bracelet, an electronic necklace, an electronic accessory, an electronic tattoo, a smart mirror, or a smart watch).

Definitions for other certain words and phrases are provided throughout this patent document. Those of ordinary skill in the art should understand that in many if not most instances, such definitions apply to prior as well as future uses of such defined words and phrases.

According to embodiments of the present disclosure, the electronic device can be a smart home appliance. Examples of the smart home appliance can include at least one of a television, a digital video disk (DVD) player, an audio player, a refrigerator, an air conditioner, a cleaner, an oven, a microwave oven, a washer, a drier, an air cleaner, a set-top box, a home automation control panel, a security control panel, a TV box (e.g., Samsung HomeSync™ APPLE TV™, or GOOGLE TV™), a gaming console (XBOX™, PLAYSTATION™), an electronic dictionary, an electronic key, a camcorder, or an electronic picture frame.

According to certain embodiments of the present disclosure, examples of the electronic device can include at least one of various medical devices (e.g., diverse portable medical measuring devices (a blood sugar measuring device, a heartbeat measuring device, or a body temperature measuring device), a magnetic resource angiography (MRA) device, a magnetic resource imaging (MRI) device, a computed tomography (CT) device, an imaging device, or an ultrasonic device), a navigation device, a global positioning system (GPS) receiver, an event data recorder (EDR), a flight data recorder (FDR), an automotive infotainment device, an sailing electronic device (e.g., a sailing navigation device or a gyro compass), avionics, security devices, vehicular head units, industrial or home robots, automatic teller's machines (ATMs), point of sales (POS) devices, or Internet of Things devices (e.g., a bulb, various sensors, an electric or gas meter, a sprinkler, a fire alarm, a thermostat, a street light, a toaster, fitness equipment, a hot water tank, a heater, or a boiler).

According to certain embodiments of the disclosure, the electronic device can be at least one of a part of a piece of furniture or building/structure, an electronic board, an electronic signature receiving device, a projector, or various measurement devices (e.g., devices for measuring water, electricity, gas, or electromagnetic waves).

According to embodiments of the present disclosure, the electronic device is one or a combination of the above-listed devices. According to embodiments of the present disclosure, the electronic device is a flexible electronic device. The electronic device disclosed herein is not limited to the above-listed devices, and can include new electronic devices depending on the development of technology.

As used herein, the term "user" may denote a human or another device (e.g., an artificial intelligent electronic device) using the electronic device.

Definitions for other certain words and phrases are provided throughout this patent document. Those of ordinary skill in the art should understand that in many if not most instances, such definitions apply to prior as well as future uses of such defined words and phrases.

BRIEF DESCRIPTION OF THE DRAWINGS

For a more complete understanding of this disclosure and its advantages, reference is now made to the following description, taken in conjunction with the accompanying drawings, in which.

DETAILED DESCRIPTION

FIGS. 1 through 12, discussed below, and the various embodiments used to describe the principles of this disclosure in this patent document are by way of illustration only and should not be construed in any way to limit the scope of the disclosure. Those skilled in the art will understand that the principles of this disclosure can be implemented in any suitably arranged wireless communication system.

Figure 1:
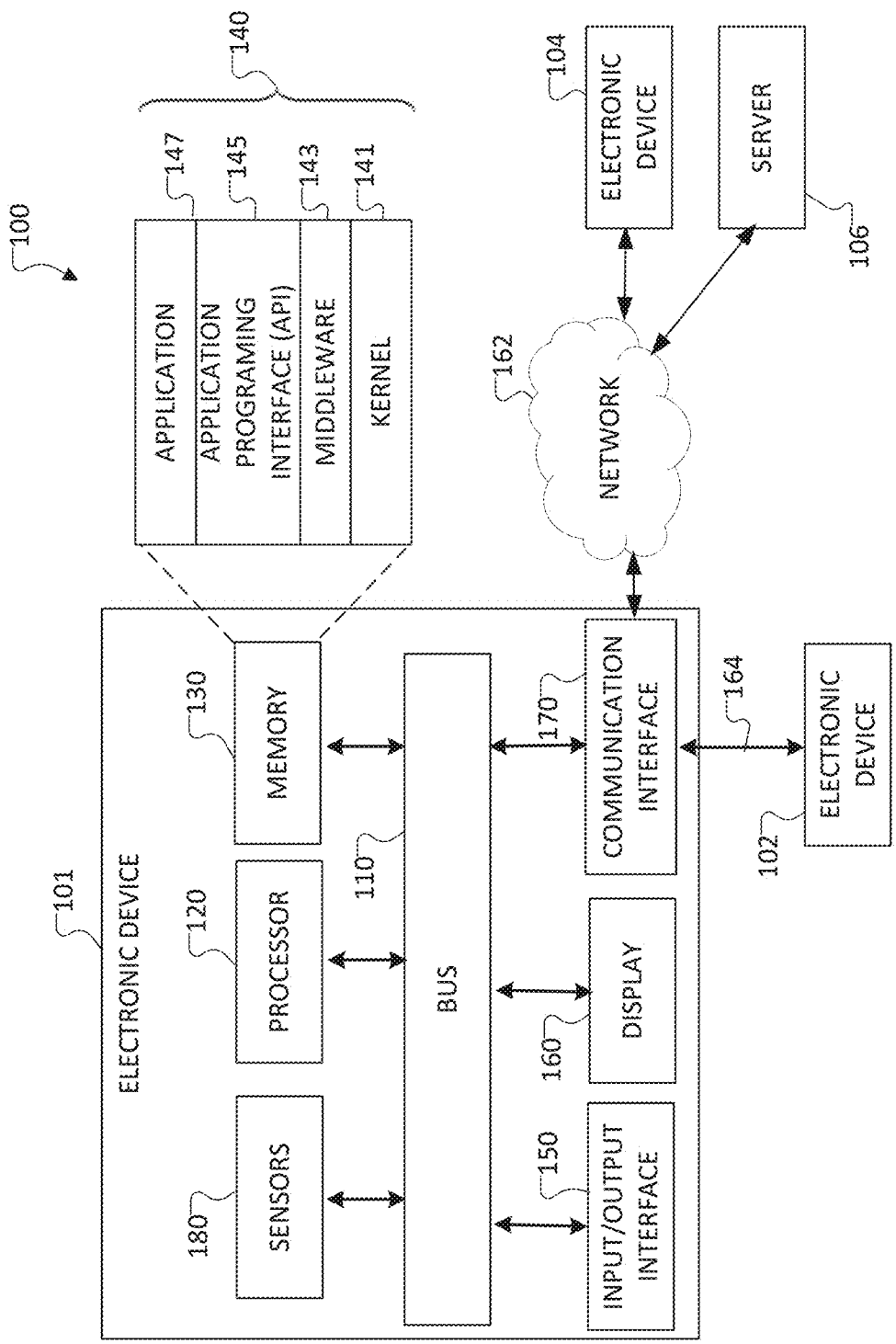
FIG. 1 illustrates an example of a network configuration according to an embodiment of this disclosure.

FIG. 1 illustrates an example network environment 100 according to various embodiments of the present disclosure. The embodiment of the network environment 100 shown in FIG. 1 is for illustration only. Other embodiments of the network environment 100 could be used without departing from the scope of this disclosure.

According to an embodiment of the present disclosure, an electronic device 101 is included in a network environment 100. The electronic device 101 can include at least one of a bus 110, a processor 120, a memory 130, an input/output (IO) interface 150, a display 160, a communication interface 170, or sensors 180. In some embodiments, the electronic device 101 can exclude at least one of the components or can add another component.

The bus 110 includes a circuit for connecting the components 120 to 170 with one another and transferring communications (e.g., control messages and/or data) between the components.

The processor 120 includes one or more of a central processing unit (CPU), an application processor (AP), or a communication processor (CP). The processor 120 is able to perform control on at least one of the other components of the electronic device 101, and/or perform an operation or data processing relating to communication.

For example, the processor 120 can receive a plurality of frames captured by the camera during a capture event. The processor 120 can identify a salient region in each of the plurality of frames. The processor 120 can determine a reference frame from the plurality of frames based on the identified salient regions. The processor 120 can fuse non-reference frames with the determined reference frame into a completed frame. The processor 120 can operate the display to display the completed frame. The processor 120 can receive a data stream of pixels from one or multiple DVS sensors or frames captured by one or multiple CMOS cameras during a capture event. In an embodiment with at least one CMOS camera, the processor 120 can identify a salient region in one or multiple frames and determine a reference frame from the one or multiple frames based on the identified salient regions.

The memory 130 can include a volatile and/or non-volatile memory. For example, the memory 130 can store commands or data related to at least one other component of the electronic device 101. In various embodiments, the memory 130 can store spatial map data that can include mapping information of a real environment such as the interior of an office building, mall, house, amusement park, neighborhood or any other real world or virtual world mapping information utilized by an application 147 on the electronic device 101. According to an embodiment of the present disclosure, the memory 130 stores software and/or a program 140. The program 140 includes, e.g., a kernel 141, middleware 143, an application programming interface (API) 145, and/or an application program (or "application") 147. At least a portion of the kernel 141, middleware 143, or API 145 can be denoted an operating system (OS).

For example, the kernel 141 can control or manage system resources (e.g., the bus 110, processor 120, or a memory 130) used to perform operations or functions implemented in other programs (e.g., the middleware 143, API 145, or application program 147). The kernel 141 provides an interface that allows the middleware 143, the API 145, or the application 147 to access the individual components of the electronic device 101 to control or manage the system resources.

The middleware 143 can function as a relay to allow the API 145 or the application 147 to communicate data with the kernel 141, for example. A plurality of applications 147 can be provided. The middleware 143 is able to control work requests received from the applications 147, e.g., by allocating the priority of using the system resources of the electronic device 101 (e.g., the bus 110, the processor 120, or the memory 130) to at least one of the plurality of applications 147.

The API 145 is an interface allowing the application 147 to control functions provided from the kernel 141 or the middleware 143. For example, the API 145 includes at least one interface or function (e.g., a command) for filing control, window control, image processing, or text control.

The IO interface 150 serve as an interface that can, e.g., transfer commands or data input from a user or other external devices to other component(s) of the electronic device 101. Further, the TO interface 150 can output commands or data received from other component(s) of the electronic device 101 to the user or the other external device.

The display 160 includes, e.g., a liquid crystal display (LCD), a light emitting diode (LED) display, an organic light emitting diode (OLED) display, or a microelectromechanical systems (MEMS) display, or an electronic paper display. The display 160 is able to display, e.g., various contents (e.g., text, images, videos, icons, or symbols) to the user. The display 160 can include a touchscreen and may receive, e.g., a touch, gesture, proximity or hovering input using an electronic pen or a body portion of the user.

For example, the communication interface 170 is able to set up communication between the electronic device 101 and an external electronic device (e.g., a first electronic device 102, a second external electronic device 104, or a server 106). For example, the communication interface 170 can be connected with the network 162 or 164 through wireless or wired communication to communicate with the external electronic device. The communication interface 170 can be a wired or wireless transceiver or any other component for transmitting and receiving signals, such as video feeds or video streams.

Electronic device 101 further includes one or more sensors 180 that can meter a physical quantity or detect an activation state of the electronic device 101 and convert metered or detected information into an electrical signal. For example, sensor 180 can include one or more buttons for touch input, a camera, a gesture sensor, a gyroscope or gyro sensor, an air pressure sensor, a magnetic sensor or magnetometer, an acceleration sensor or accelerometer, a depth or distance sensor, a grip sensor, a proximity sensor, a color sensor (e.g., a red green blue (RGB) sensor), a bio-physical sensor, a temperature sensor, a humidity sensor, an illumination sensor, an ultraviolet (UV) sensor, an electromyography (EMG) sensor, an electroencephalogram (EEG) sensor, an electrocardiogram (ECG) sensor, an IR sensor, an ultrasound sensor, an iris sensor, a fingerprint sensor, etc. The sensor(s) 180 can further include a control circuit for controlling at least one of the sensors included therein. Any of these sensor(s) 180 can be located within the electronic device 101. In some embodiments, a camera sensor 180 can capture a plurality of frames for a single image to be combined by the processor 120. In some embodiments, the camera sensor 180 (for example, a DVS camera) can capture a stream of DVS pixels to be processed by the processor 120.

The first external electronic device 102 or the second external electronic device 104 can be a wearable device (for example, smart glasses, smart watch, etc.) or an electronic device 101-mountable wearable device (e.g., an optical head mounted display (HMD), an HMD that mounts or includes the electronic device 101, etc.). When the electronic device 101 is mounted in a HMD (e.g., the electronic device 102), the electronic device 101 is able to detect the mounting in the HMD and operate in an augmented reality mode (or a virtual reality mode, a cross reality mode, an extended reality mode, etc.). In certain embodiments, the electronic device 101 is able to detect the mounting in the HMD and operate in an augmented reality mode. When the electronic device 101 is mounted in the electronic device 102 (e.g., the HMD), the electronic device 101 can communicate with the electronic device 102 through the communication interface 170. The electronic device 101 can be directly connected with the electronic device 102 to communicate with the electronic device 102 without involving a separate network.

The wireless communication is able to use at least one of, e.g., long term evolution (LTE), long term evolution-advanced (LTE-A), 5th generation wireless system (5G), mm-wave or 60 GHz wireless communication, Wireless USB, code division multiple access (CDMA), wideband code division multiple access (WCDMA), universal mobile telecommunication system (UMTS), wireless broadband (Wi-Bro), or global system for mobile communication (GSM), as a cellular communication protocol. The wired connection can include at least one of universal serial bus (USB), high definition multimedia interface (HDMI), recommended standard 232 (RS-232), or plain old telephone service (POTS).

The network 162 includes at least one of communication networks. Examples of communication include a computer network (e.g., local area network (LAN) or wide area network (WAN)), Internet, or a telephone network.

The first and second external electronic devices 102 and 104 and server 106 each can be a device of the same or a different type from the electronic device 101. According to certain embodiments of the present disclosure, the server 106 includes a group of one or more servers. According to certain embodiments of the present disclosure, all or some of operations executed on the electronic device 101 can be executed on another or multiple other electronic devices (e.g., the electronic devices 102 and 104 or server 106). According to certain embodiments of the present disclosure, when the electronic device 101 should perform some function or service automatically or at a request, the electronic device 101, instead of executing the function or service on its own or additionally, can request another device (e.g., electronic devices 102 and 104 or server 106) to perform at least some functions associated therewith. The other electronic device (e.g., electronic devices 102 and 104 or server 106) is able to execute the requested functions or additional functions and transfer a result of the execution to the electronic device 101. The electronic device 101 can provide a requested function or service by processing the received result as it is or additionally. To that end, a cloud computing, distributed computing, or client-server computing technique can be used, for example.

Although FIG. 1 shows that the electronic device 101 includes the communication interface 170 to communicate with the external electronic device 104 or server 106 via the network 162, the electronic device 101 can be independently operated without a separate communication function, according to an embodiment of the present disclosure.

The server 106 can support to drive the electronic device 101 by performing at least one of operations (or functions) implemented on the electronic device 101. For example, the server 106 can include a processing module or processor that may support the processor 120 implemented in the electronic device 101.

For example, the electronic device 101 can include an event processing module, such as within processor 120. The event processing module can process at least part of information obtained from other elements (e.g., the processor 120, the memory 130, the input/output interface 150, or the communication interface 170) and can provide the same to the user in various manners. The server event processing module can include at least one of the components of the event processing module and perform (or instead perform) at least one of the operations (or functions) conducted by the event processing module.

For example, according to an embodiment of the present disclosure, the event processing module processes information related to an event, which is generated while the electronic device 101 is mounted in a wearable device (e.g., the electronic device 102) to function as a display apparatus and to operate in the augmented reality mode, to fit the augmented reality mode and display the processed information. When the event generated while operating in the augmented reality mode is an event related to running an application, the event processing module can block the running of the application or process the application to operate as a background application or process. Additional information on the event processing module 185 may be provided through FIG. 2 described below.

The event processing module can be separate from the processor 120 or at least a portion of the event processing module can be included or implemented in the processor 120 or at least one other module, or the overall function of the event processing module can be included or implemented in the processor 120 shown or another processor. The event processing module can perform operations according to embodiments of the present disclosure in interoperation with at least one program 140 stored in the memory 130.

Figure 2:
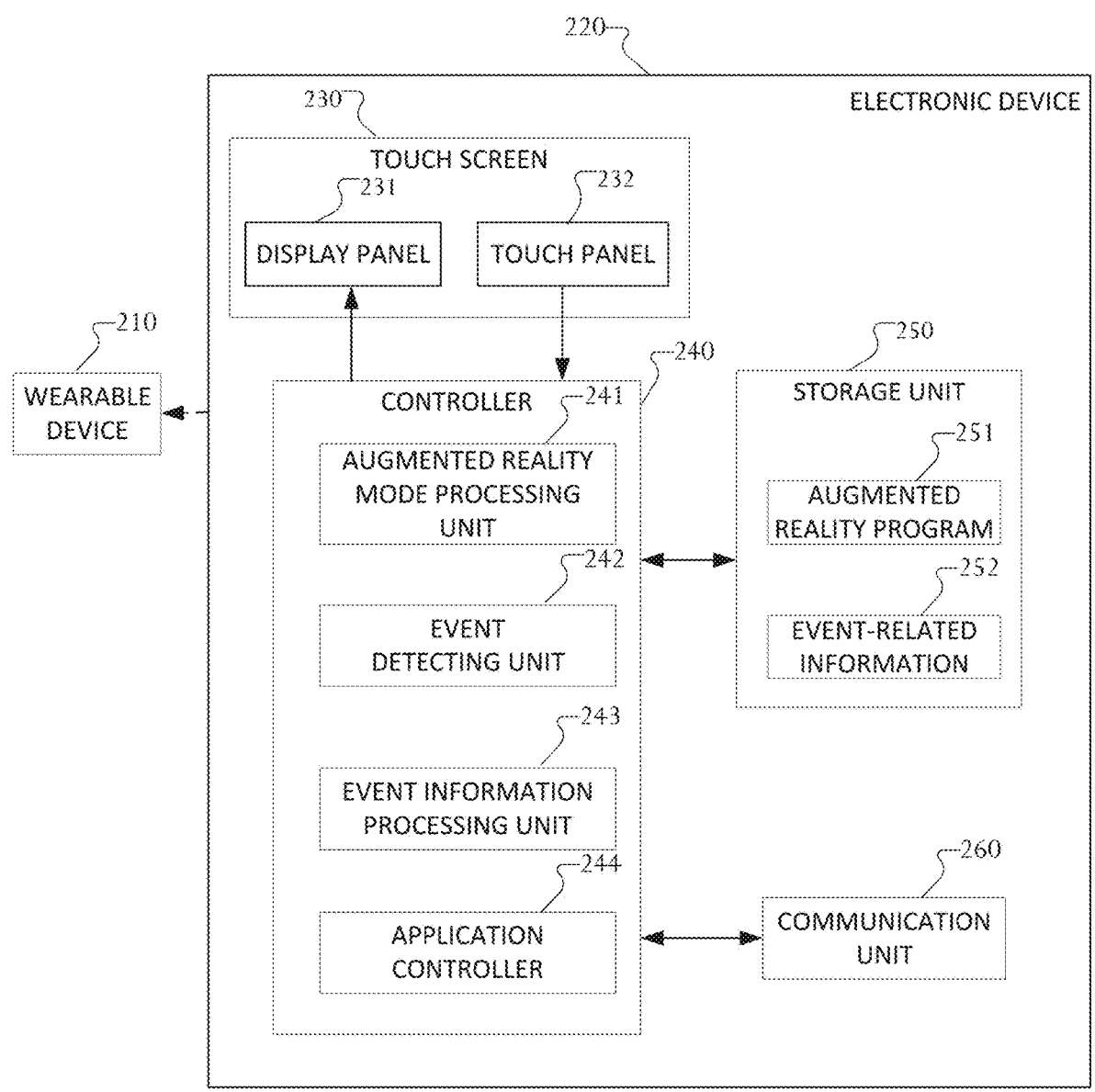
FIG. 2 is a block diagram of an example configuration of an electronic device according to an embodiment of this disclosure.

FIG. 2 illustrates an example electronic device 220 according to various embodiments of the present disclosure. The embodiment of the electronic device 220 shown in FIG. 2 is for illustration only. Other embodiments of electronic device 220 could be used without departing from the scope of this disclosure. In the example shown in FIG. 2, although an augmented reality (AR) system is depicted, at least some embodiments of the present disclosure apply equally to a virtual reality (VR) and the augmented reality (AR). Collectively the various reality scenarios can be referenced herein as extended reality (XR). The electronic device 220 depicted in FIG. 2 can be configured the same as, or similar to, any of electronic devices 101, 102, or 104.

FIG. 2 is a block diagram illustrating an example configuration of an electronic device according to an embodiment of the present disclosure. Referring to FIG. 2, the electronic device 220 according to an embodiment of the present disclosure can be an electronic device 220 having at least one display. In the following description, the electronic device 220 can be a device primarily performing a display function or can denote a normal electronic device including at least one display. For example, the electronic device 220 can be an electronic device (e.g., a smartphone) having a touchscreen 230.

According to certain embodiments, the electronic device 220 can include at least one of a touchscreen 230, a controller 240, a storage unit 250, or a communication unit 260. The touchscreen 230 can include a display panel 231 and/or a touch panel 232. The controller 240 can include at least one of an augmented reality mode processing unit 241 (e.g., an XR mode processing unit), an event determining unit 242, an event information processing unit 243, or an application controller 244.

For example, when the electronic device 220 is mounted in a wearable device 210, the electronic device 220 can operate, e.g., as an HMD, and run an augmented reality mode. Further, according to an embodiment of the present disclosure, even when the electronic device 220 is not mounted in the wearable device 210, the electronic device 220 can run the augmented reality mode according to the user's settings or run an augmented reality mode related application. In the following embodiment, although the electronic device 220 is set to be mounted in the wearable device 210 to run the augmented reality mode, embodiments of the present disclosure are not limited thereto.

According to certain embodiments, when the electronic device 220 operates in the augmented reality mode (e.g., the electronic device 220 is mounted in the wearable device 210 to operate in a head mounted theater (HMT) mode), two screens corresponding to the user's eyes (left and right eye) can be displayed through the display panel 231.

According to certain embodiments, when the electronic device 220 is operated in the augmented reality mode, the controller 240 can control the processing of information related to an event generated while operating in the augmented reality mode to fit in the augmented reality mode and display the processed information. According to certain embodiments, when the event generated while operating in the augmented reality mode is an event related to running an application, the controller 240 can block the running of the application or process the application to operate as a background process or application.

More specifically, according to an embodiment of the present disclosure, the controller 240 can include at least one of an augmented reality mode processing unit 241, an event determining unit 242, an event information processing unit 243, or an application controller 244 to perform functions according to various embodiments of the present disclosure. An embodiment of the present disclosure can be implemented to perform various operations or functions as described below using at least one component of the electronic device 220 (e.g., the touchscreen 230, controller 240, or storage unit 250).

According to certain embodiments, when the electronic device 220 is mounted in the wearable device 210 or the augmented reality mode is run according to the user's setting or as an augmented reality mode-related application runs, the augmented reality mode processing unit 241 can process various functions related to the operation of the augmented reality mode. The augmented reality mode processing unit 241 can load at least one augmented reality program 251 stored in the storage unit 250 to perform various functions.

The event detecting unit 242 determines or detects that an event is generated while operated in the augmented reality mode by the augmented reality mode processing unit 241. Further, the event detecting unit 242 can determine whether there is information to be displayed on the display screen in relation with an event generated while operating in the augmented reality mode. Further, the event detecting unit 242 can determine that an application is to be run in relation with an event generated while operating in the augmented reality mode. Various embodiments of an application related to the type of event are described below.

The event information processing unit 243 can process the event-related information to be displayed on the display screen to fit the augmented reality mode when there is information to be displayed in relation with an event occurring while operating in the augmented reality mode depending on the result of determination by the event detecting unit 242. Various methods for processing the event-related information can apply. For example, when a three-dimensional (3D) image is implemented in the augmented reality mode, the electronic device 220 converts the event-related information to fit the 3D image. For example, event-related information being displayed in two dimensions (2D) can be converted into left and right eye information corresponding to the 3D image, and the converted information can then be synthesized and displayed on the display screen of the augmented reality mode being currently run.

When it is determined by the event detecting unit 242 that there is an application to be run in relation with the event occurring while operating in the augmented reality mode, the application controller 244 performs control to block the running of the application related to the event. According to certain embodiments, when it is determined by the event detecting unit 242 that there is an application to be run in relation with the event occurring while operating in the augmented reality mode, the application controller 244 can perform control so that the application is run in the background so as not to influence the running or screen display of the application corresponding to the augmented reality mode when the event-related application runs.

The storage unit 250 can store an augmented reality program 251. The augmented reality program 251 can be an application related to the augmented reality mode operation of the electronic device 220. The storage unit 250 can also store the event-related information 252. The event detecting unit 242 can reference the event-related information 252 stored in the storage unit 250 in order to determine whether the occurring event is to be displayed on the screen or to identify information on the application to be run in relation with the occurring event.

The wearable device 210 can be an electronic device including at least one function of the electronic device 101 shown in FIG. 1, and the wearable device 210 can be a wearable stand to which the electronic device 220 can be mounted. In case the wearable device 210 is an electronic device, when the electronic device 220 is mounted on the wearable device 210, various functions can be provided through the communication unit 260 of the electronic device 220. For example, when the electronic device 220 is mounted on the wearable device 210, the electronic device 220 can detect whether to be mounted on the wearable device 210 for communication with the wearable device 210 and can determine whether to operate in the augmented reality mode (or an HMT mode).

According to certain embodiments, upon failure to automatically determine whether the electronic device 220 is mounted when the communication unit 260 is mounted on the wearable device 210, the user can apply various embodiments of the present disclosure by running the augmented reality program 251 or selecting the augmented reality mode (or, the HMT mode). According to an embodiment of the present disclosure, when the wearable device 210 functions with or as part the electronic device 101, the wearable device can be implemented to automatically determine whether the electronic device 220 is mounted on the wearable device 210 and enable the running mode of the electronic device 220 to automatically switch to the augmented reality mode (or the HMT mode).

At least some functions of the controller 240 shown in FIG. 2 can be included in the event processing module 185 or processor 120 of the electronic device 101 shown in FIG. 1. The touchscreen 230 or display panel 231 shown in FIG. 2 can correspond to the display 160 of FIG. 1. The storage unit 250 shown in FIG. 2 can correspond to the memory 130 of FIG. 1.

Although in FIG. 2 the touchscreen 230 includes the display panel 231 and the touch panel 232, according to an embodiment of the present disclosure, the display panel 231 or the touch panel 232 may also be provided as a separate panel rather than being combined in a single touchscreen 230. Further, according to an embodiment of the present disclosure, the electronic device 220 can include the display panel 231, but exclude the touch panel 232.

According to certain embodiments, the electronic device 220 can be denoted as a first device (or a first electronic device), and the wearable device 210 may be denoted as a second device (or a second electronic device) for ease of description.

According to certain embodiments, an electronic device can comprise a display unit displaying on a screen corresponding to an augmented reality mode and a controller performing control that detects an interrupt according to an occurrence of at least one event, that varies event-related information related to the event in a form corresponding to the augmented reality mode, and that displays the varied event-related information on the display screen that corresponds to the augmented reality mode.

According to certain embodiments, the event can include any one or more selected from among a call reception event, a message reception event, an alarm notification, a scheduler notification, a wireless fidelity (Wi-Fi) connection, a WiFi disconnection, a low battery notification, a data permission or use restriction notification, a no application response notification, or an abnormal application termination notification.

According to certain embodiments, the electronic device further comprises a storage unit configured for storing the event-related information when the event is not an event to be displayed in the augmented reality mode, wherein the controller can perform control to display the event-related information stored in the storage unit when the electronic device switches from the virtual reality mode into an augmented reality mode or a see-through (non-augmented reality) mode. According to certain embodiments, the electronic device can further comprise a storage unit that stores information regarding at least one event to be displayed in the augmented reality mode. According to certain embodiments, the event can include an instant message reception notification event. According to certain embodiments, when the event is an event related to running at least one application, the controller can perform control that blocks running of the application according to occurrence of the event. According to certain embodiments, the controller can perform control to run the blocked application when a screen mode of the electronic device switches from a virtual reality mode into an augmented reality mode or a see-through (non-augmented reality) mode. According to certain embodiments, when the event is an event related to running at least one application, the controller can perform control that enables the application, according to the occurrence of the event, to be run on a background of a screen of the augmented reality mode. According to certain embodiments, when the electronic device is connected with a wearable device, the controller can perform control to run the augmented reality mode. According to certain embodiments, the controller can enable the event-related information to be arranged and processed to be displayed in a three dimensional (3D) space of the augmented reality mode screen being displayed on a current display screen. According to certain embodiments, the electronic device 220 can include additional sensors such as one or more complementary metal-oxide semiconductor (CMOS) cameras, dynamic vision sensor (DVS) cameras, 360 degree cameras, or a combination thereof. In certain embodiments, the CMOS camera can be a red, green, blue (RGB) camera.

Figure 3:
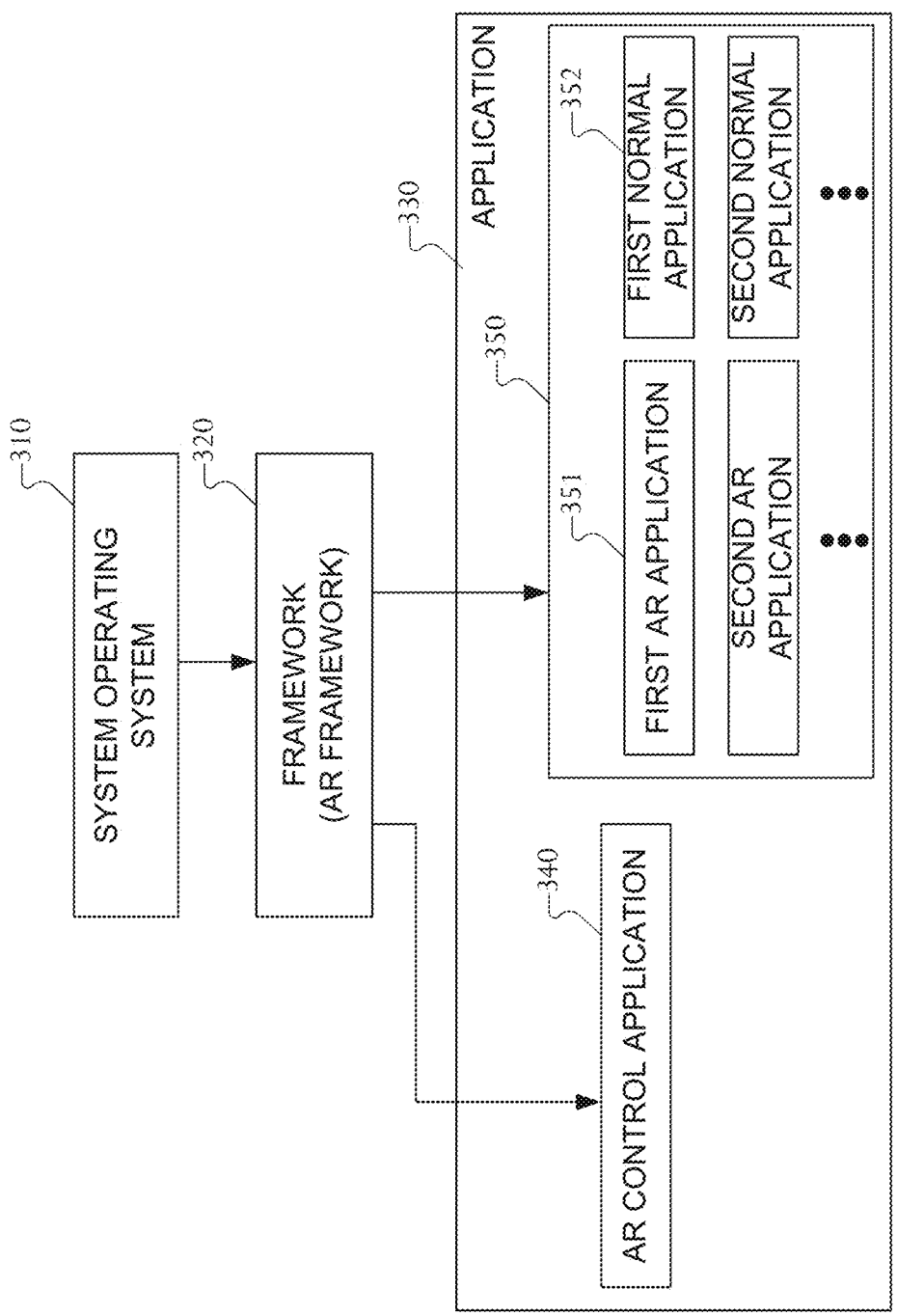
FIG. 3 is a block diagram that illustrates a program module according to an embodiment of this disclosure.
Figure 4A:
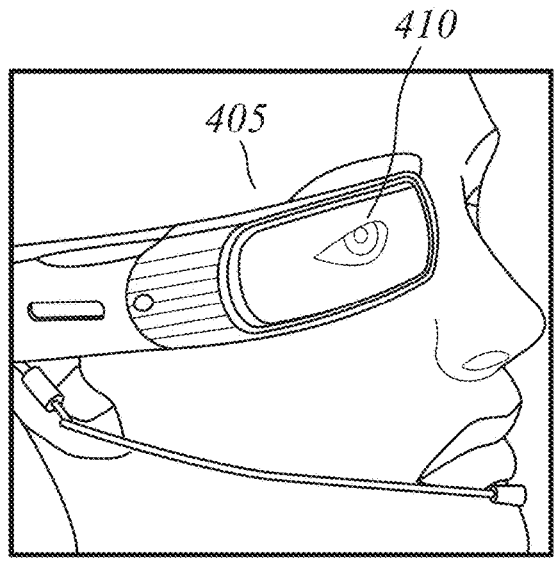
FIGS. 4A, 4B, 4C, and 4D illustrate examples of a head mounted display (HMD) for use in augmented reality, mixed reality, or virtual reality according to an embodiment of this disclosure.
Figure 4B:
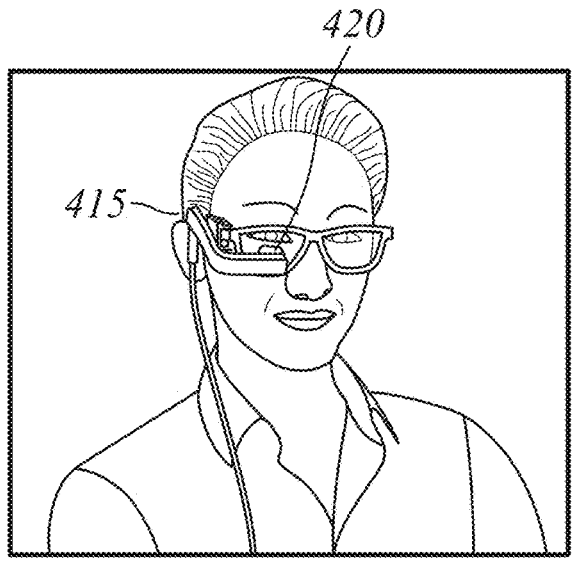
Figure 4C:
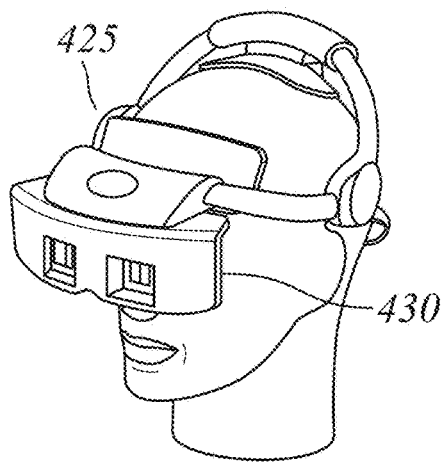
Figure 4D:
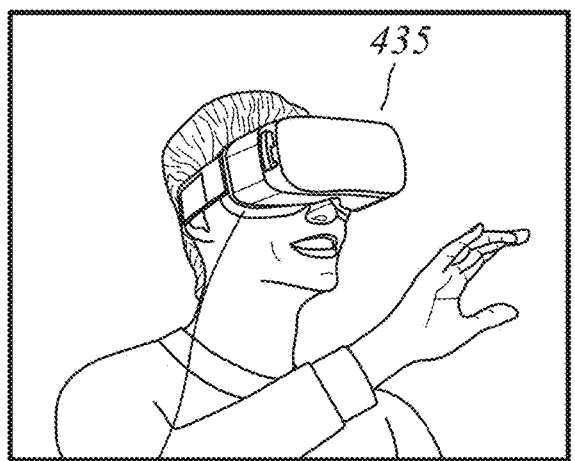

FIG. 3 is a block diagram illustrating a program module according to an embodiment of the present disclosure. The embodiment illustrated in FIG. 3 is for illustration only and other embodiments could be used without departing from the scope of the present disclosure. In the example shown in FIG. 3, although an augmented reality (AR) system is depicted, at least some embodiments of the present disclosure apply equally to a virtual reality (VR) and the augmented reality (AR). Collectively the various reality scenarios can be referenced herein as extended reality (XR). Referring to FIG. 3, the program module can include a system operating system (e.g., an OS) 310, a framework 320, and an application(s) 330.

The system operating system 310 can include at least one system resource manager or at least one device driver. The system resource manager can perform, for example, control, allocation, or recovery of the system resources. The system resource manager may include at least one manager, such as a process manager, a memory manager, or a file system manager. The device driver may include at least one driver, such as, for example, a display driver, a camera driver, a Bluetooth driver, a shared memory driver, a USB driver, a keypad driver, a Wi-Fi driver, an audio driver, or an inter-process communication (IPC) driver.

According to certain embodiments, the framework 320 (e.g., middleware) can provide, for example, functions commonly required by an application or provide the application with various functions through an application programming interface (API) to allow the application to efficiently use limited system resources inside the electronic device.

The AR framework included in the framework 320 can control functions related to augmented reality mode operations on the electronic device. For example, when running an augmented reality mode operation, the AR framework 320 can control at least one AR application 351, which is related to augmented reality, among applications 330 so as to provide the augmented reality mode on the electronic device.

The application(s) 330 can include a plurality of applications and can include at least one AR application 351 running in the augmented-reality mode and at least one normal application 352 running in a non-augmented-reality mode.

The application(s) 330 can further include an AR control application 340. An operation of the at least one AR application 351 and/or at least one normal application 352 can be controlled by the AR control application 340.

Again, although the AR framework, the at least one AR application, the AR mode, and the AR control application are discussed above, it is contemplated at least some embodiments of the present disclosure apply equally to virtual reality (VR), mixed reality (MR), or another cross/extended reality (XR) environment.

When at least one event occurs while the electronic device operates in the augmented reality mode, the system operating system 310 can notify the framework 320, for example the AR framework, of an occurrence of an event.

The framework 320 can then control the running of the normal application 352 so that event-related information can be displayed on the screen for the event occurring in the non-augmented reality mode, but not in the augmented reality mode. When there is an application to be run in relation with the event occurring in the normal mode, the framework 320 can perform or provide control to run at least one normal application 352.

According to certain embodiments, when an event occurs while operating in the augmented reality mode, the framework 320, for example the AR framework, can block the operation of at least one normal application 352 to display the information related to the occurring event. The framework 320 can provide the event occurring, while operating in the augmented reality mode, to the AR control application 340.

The AR control application 340 can process the information related to the event occurring while operating in the augmented reality mode to fit within the operation of the augmented reality mode. For example, a 2D, planar event-related information can be processed into 3D information.

The AR control application 340 can control at least one AR application 351 currently running and can perform control to synthesize the processed event-related information for display on the screen being run by the AR application 351 and display the result of the event related information thereon.

According to certain embodiments, when an event occurs while operating in the augmented reality mode, the framework 320 can perform control to block the running of at least one normal application 352 related to the occurring event.

According to certain embodiments, when an event occurs while operating in the augmented reality mode, the framework 320 can perform control to temporarily block the running of at least one normal application 352 related to the occurring event, and then when the augmented reality mode terminates, the framework 320 can perform control to run the blocked normal application 352.

According to certain embodiments, when an event occurs while operating in the augmented reality mode, the framework 320 can control the running of at least one normal application 352 related to the occurring event so that the at least one normal application 352 related to the event operates in the background so as not to influence the screen used by the AR application 351 currently running.

Embodiments described in connection with FIG. 3 are examples for implementing an embodiment of the present disclosure in the form of a program, and embodiments of the present disclosure are not limited thereto and rather can be implemented in other various forms. Further, while the embodiment described in connection with FIG. 3 references AR, it can be applied to other scenarios such as mixed reality, or virtual reality etc. Collectively the various reality scenarios can be referenced herein as extended reality (XR).

Various examples of aspects of a user interface (UI) for XR scenarios. It should be noted that aspects of XR UIs disclosed herein are merely examples of XR UIs and are not intended to be limiting.

There are different types of display elements that can be used in XR scenarios. For example, displayed elements are either tied directly to the real world or tied loosely to the XR display space. In-world elements are elements that move in relation to the real or virtual environment itself (i.e., move in relation to the environment itself). Depending on the object, in-world elements may not necessarily move in relation to the user's head when wearing a head mounted display (HMD).

Heads up display (HUD) elements are elements wherein users can make small head movements to gaze or look directly at various application (app) elements without moving the HUD elements container or UI panel in the display view. HUD elements can be a status bar or UI by which information is visually displayed to the user as part of the display.

FIGS. 4A, 4B, 4C, and 4D illustrate examples of a head mounted display (HMD) for use in augmented reality, mixed reality, or virtual reality according to an embodiment of this disclosure. The embodiments of the HMDs shown in FIGS. 4A-4D are for illustration only and other configurations could be used without departing from the scope of the present disclosure.

The HMD can generate an augmented reality environment in which a real-world environment is rendered with augmented information. The HMD can be monocular or binocular and can be an opaque, transparent, semi-transparent or reflective device. For example, the HMD can be a monocular electronic device 405 having a transparent screen 410. A user is able to see through the screen 410 as well as able to see images rendered, projected or displayed on the screen 410. The images may be projected onto the screen 410, generated or rendered by the screen 410 or reflected on the screen 410. In certain embodiments, the HMD is a monocular electronic device 415 having an opaque or non-see through display 420. The non-see through display 420 can be a liquid crystal display (LCD), a Light emitting diode (LED), active-matrix organic light emitting diode (AMO-LED), or the like. The non-see through display 420 can be configured to render images for viewing by the user. In certain embodiments, the HMD can be a binocular electronic device 425 having a transparent screen 430. The transparent screen 430 can be a single contiguous screen, such as adapted to be viewed by, or traverse across, both eyes of the user. The transparent screen 430 also can be two transparent screens in when one screen is disposed corresponding to a respective eye of the user. The user is able to see through the screen 430 as well as able to see images rendered, projected or displayed on the screen 430. The images may be projected onto the screen 430, generated or rendered by the screen 430 or reflected on the screen 430. In certain embodiments, the HMD is a binocular electronic device 435 having an opaque or non-see through display 440. The HMD can include a camera or camera input configured to capture real-world information and display, via the non-see through display 440, real-world information. The non-see through display 440 can be an LCD, LED, AMOLED, or the like. The non-see through display 440 can be configured to render images for viewing by the user. The real-world information captured by the camera can be rendered as a video image on the display with augmented information.

Embodiments of the present disclosure relate to gaze tracking for use in augmented reality (AR), virtual reality (VR), mixed reality (MR) or another cross/extended reality (XR) systems. In the recent years, a significant increase in interest in Augmented Reality (AR) glasses (as well as VR headsets, MR Head Mounted Displays, and the like) has been experienced. Eye tracking can, in some cases, be achieved with conventional cameras and infrared illumination, but this approach requires a large amount of processing power. In turn, a significant issue with conventional HMDs is a very high cost incurred as a result of the large amount of processing power required. While a conventional camera, without an illumination system, can be utilized, the dynamic range is usually unsuitable for recognizing objects (for example, eye movement) in the dark. Conventional cameras also require a high frame rate to be able to track eye movement accurately.

Embodiments of the present disclosure provide a system and method that includes one or more dynamic vision sensor (DVS) cameras to detect eye movement based on changes of pixel intensity to enable eye tracking and blink detection. DVS cameras have the advantage of being reliable, low-cost, low-power, and having a wide dynamic range (for example, approximately 120 dB), which makes tracking in darker environment possible without additional sources of light (for example, infrared illumination, external lighting, and so forth). Certain embodiments provide additional benefits from utilizing a DVS camera having a very low latency (for example, approximately 1000 Hertz (Hz)), which can reduce or eliminate motion blur. In certain embodiments, the DVS camera is well suited to detect objects in motion, especially one or more borders/edges of objects, as intensity changes occur primarily at the border(s)/edges(s) of a moving object.

Embodiments of the present disclosure also provide a system and method that utilizes one or more DVS cameras in conjunction with one or more CMOS cameras to track eye movement. Certain embodiments of the present disclosure provide a system and method that utilizes one or more CMOS cameras to be turned on during an initialization phase of the eye tracking system. Certain embodiments of the present disclosure also can include one or more illumination sources to be used in conjunction with the CMOS cameras to perform eye/iris/pupil detection, user recognition and gaze pose estimation (for example, initial eye tracking). Certain embodiments can use the one or more illumination sources in conjunction with the DVS cameras to perform gaze pose estimation (for example, post-initialization eye tracking).

Figures 5A, 5B, 5C:
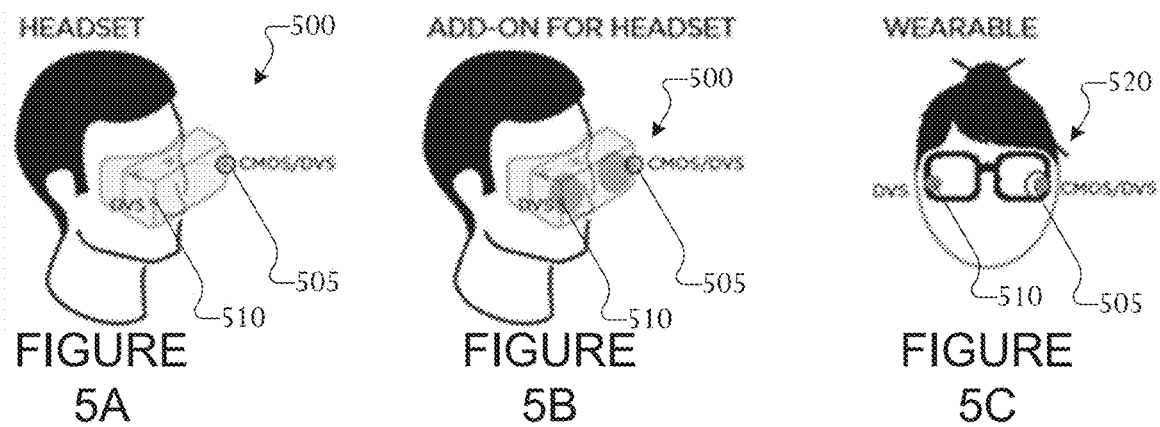
FIGS. 5A, 5B and 5C illustrate examples of the placement of dynamic vision sensor (DVS) cameras and complementary metal oxide semiconductor (CMOS) cameras in various HMDs for use in augmented reality, mixed reality, or virtual reality according to embodiments of the present disclosure.

FIGS. 5A, 5B, and 5C illustrate camera positions for use in various headsets according to embodiments of the present disclosure. The embodiments shown in FIGS. 5A-5C are for illustration only and other configurations could be used without departing from the scope of the present disclosure. An HMD 500 depicted in FIGS. 5A-5C can be configured the same as, or similar to, any of HMD 405, 415, 425, or 435 shown in FIGS. 4A-4D respectively. The HMD 500 includes both a CMOS camera 505 and a DVS camera 510. Although embodiments having one camera, or one camera system could be used without departing from the scope of the present disclosure.

In certain embodiments, each of the CMOS camera 505 and the DVS camera 510 are "built-in" or permanently attached to the HMD 500. In the example shown in FIG. 5A, the HMD 500 includes the CMOS camera 505 and the DVS camera 510 as integrated components of the HMD 500. The CMOS camera 505 is disposed on a first inward facing side of the HMD 500 and the DVS camera 510 is disposed on a second inward facing side of the HMD 500. The CMOS camera 505 and DVS camera 510 can be disposed on or adjacent to a display screen of the HMD 500 or on or adjacent to a lens surface of the HMD 500. Each of the CMOS camera 505 and DVS camera 510 is positioned to "see" or direct toward (and, in some embodiments, to capture an image, or one or more pixels, representative of at least a portion of) a respective eye of a wearer of the HMD 500 when the HMD 500 is worn. Although the CMOS camera 505 is illustrated corresponding to a left eye of the wearer and the DVS camera 510 is illustrated corresponding to a right eye of the wearer, embodiments in which the DVS camera 510 is disposed corresponding to the left eye or the CMOS camera 505 is disposed corresponding to right eye could be used. In certain embodiments, each of the CMOS camera 505 and DVS camera 510 is disposed to capture features of a different eye. For example, the CMOS camera 505 can be disposed to capture light changes of (for example, image or pixel information representative of) the left eye of the wearer while the DVS camera 510 can be disposed to capture light changes of (for example, image or pixel information representative of) the right eye of the wearer.

In certain embodiments, one or both of the CMOS camera 505 and the DVS camera 510 are "added-on" to or removably coupled to the HMD 500. In the example shown in FIG. 5B, the CMOS camera 505 and DVS camera 510 are removably attached to the HMD 500. The CMOS camera 505 and the DVS camera 510 can be attached at predetermined positions, such as via an existing coupling on the HMD 500. In certain embodiments, one or more of the CMOS camera 505 and the DVS camera 510 include a coupling means, such as an adhesive or magnetic interface, that enables a respective CMOS camera 505 or the DVS camera 510 to be attached to the HMD 500, even if the HMD 500 does not include a coupling means. In certain embodiments, one or more of the CMOS camera 505 and the DVS camera 510 include a physical attachment configured to engage an aspect of the structure of the HMD 500. For example, the physical attachment can be an elastic strap or fitted edge configured to "snap to" or grip one or more edge surfaces of the HMD 500. In certain embodiments, the coupling means includes an electrical or data interface configured to enable communications between processing circuitry in the one or more of the CMOS camera 505 and the DVS camera 510 and processing circuitry in the HMD 500. In certain embodiments, one or more of the CMOS camera 505 and the DVS camera 510 include a near-field communication transceiver and/or another transceiver (for example, a BLUETOOTH transceiver), configured to communicate data between processing circuitry in the one or more of the CMOS camera 505 and the DVS camera 510 and processing circuitry in the HMD 500.

In certain embodiments, one or both of the CMOS camera 505 and the DVS camera 510 are included in, or adapted to be "added-on" to or removably coupled to a wearable device 520. The example shown in FIG. 5C illustrates a wearable device 520 that includes the CMOS camera 505 and the DVS camera 510. The wearable device 520 can be, for example, smart glasses. In certain embodiments, the wearable device 520 includes the CMOS camera 505 and the DVS camera 510 as "built-in" components. For example, the CMOS camera 505 and the DVS camera 510 can be permanently attached as part of the wearable device 520. In certain embodiments, the CMOS camera 505 and the DVS camera 510 are removably coupled to the wearable device 520. For example, the CMOS camera 505 and the DVS camera 510 can be attached at predetermined positions, such as via an existing coupling on the wearable device 520. In certain embodiments, one or more of the CMOS camera 505 and the DVS camera 510 include a coupling means, such as an adhesive or magnetic interface, that enables a respective CMOS camera 505 or the DVS camera 510 to be attached to the wearable device 520, even if the wearable device 520 does not include a coupling means. In certain embodiments, the one or more of the CMOS camera 505 and the DVS camera 510 include a physical attachment configured to engage an aspect of the structure of the wearable device 520. For example, the physical attachment can be an elastic strap or fitted edge configured to "snap to" or grip one or more edge surfaces or one or more arms of the wearable device 520. In certain embodiments, the coupling means includes an electrical or data interface configured to enable communications between processing circuitry in the one or more of the CMOS camera 505 and the DVS camera 510 and processing circuitry in the wearable device 520. In certain embodiments, one or more of the CMOS camera 505 and the DVS camera 510 include a near-field communication transceiver and/or another transceiver (for example, a BLUETOOTH transceiver), configured to communicate data between processing circuitry in the one or more of the CMOS camera 505 and the DVS camera 510 and processing circuitry in the wearable device 520.

The wearable devices 520 can enhance or augment reality by highlighting one or more areas where a user is looking. For example, embodiments of the wearable devices 520 can provide digital/virtual coupons or information when the user is looking at a product in a supermarket. Additionally, another camera directed toward a scene, or view, at which the user is looking can perform smart recognition, such as a recognition of objects, such as products or obstacles. In certain embodiments, the wearable device 520 is configured to enable appropriate/correct alignment of the lenses with the user's eyes.

In certain embodiments of the present disclosure, AR headsets/HMDs having one or more of the CMOS camera 505 and the DVS camera 510 coupled thereto can provide for low-cost rendering on smartphones/mobile devices by using foveated rendering. Embodiments of the present disclosure also enable appropriate/correct alignment of the lenses with the eyes of the wearer. Additional embodiments of the present disclosure can provide for a more immersive gaming experience, than with conventional technology, since a gaze position of the wearer can be determined more efficiently.

Figure 6:
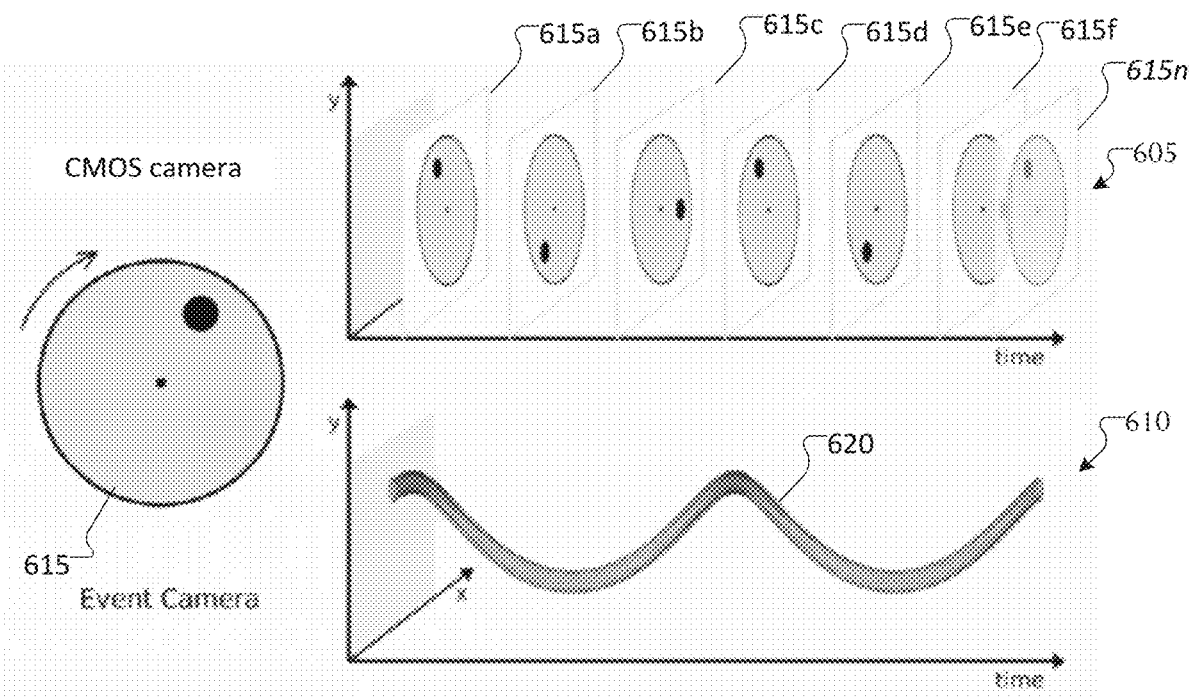
FIG. 6 illustrates a comparison between a complementary metal oxide semiconductor (CMOS) camera and an event camera according to embodiments of the present disclosure.

FIG. 6 illustrates a comparison between complementary metal oxide semiconductor (CMOS) camera output 605 and an event camera output 610 according to embodiments of the present disclosure. The graphs of the CMOS camera output 605 and the event camera output 610 are for illustration only and other examples and illustrations could be used without departing from the scope of the present disclosure. In the example shown in FIG. 6, a circle with rotational movement 615 is tracked along an x, y, t (time) coordinate system.

The CMOS output 605, as depicted on the x,y,t coordinate system, is a frame by frame capture of the circle movement 615. Evaluating successive frames 615-615$n$ can be inefficient because each frame contains an enormous amount of redundant information, which can waste memory access and storage, energy computational power, and time as it is waiting for unnecessary frames. Additionally, since each frame also imposes the same exposure time on every pixel, the processing of scenes containing very dark and very bright regions is nearly impossible. Event camera output 610, as depicted on the x,y,t coordinate system, captures and transmits a stream 620 of pixel data. In certain embodiment, the DVS camera captures only a change in pixel intensity, such as caused by the circle movement 615. By capturing a change in pixel intensity, the DVS camera is able to produce a stream of asynchronous pixels-on events (or DVS-on pixel events) at microsecond time resolution.

Figure 7A:
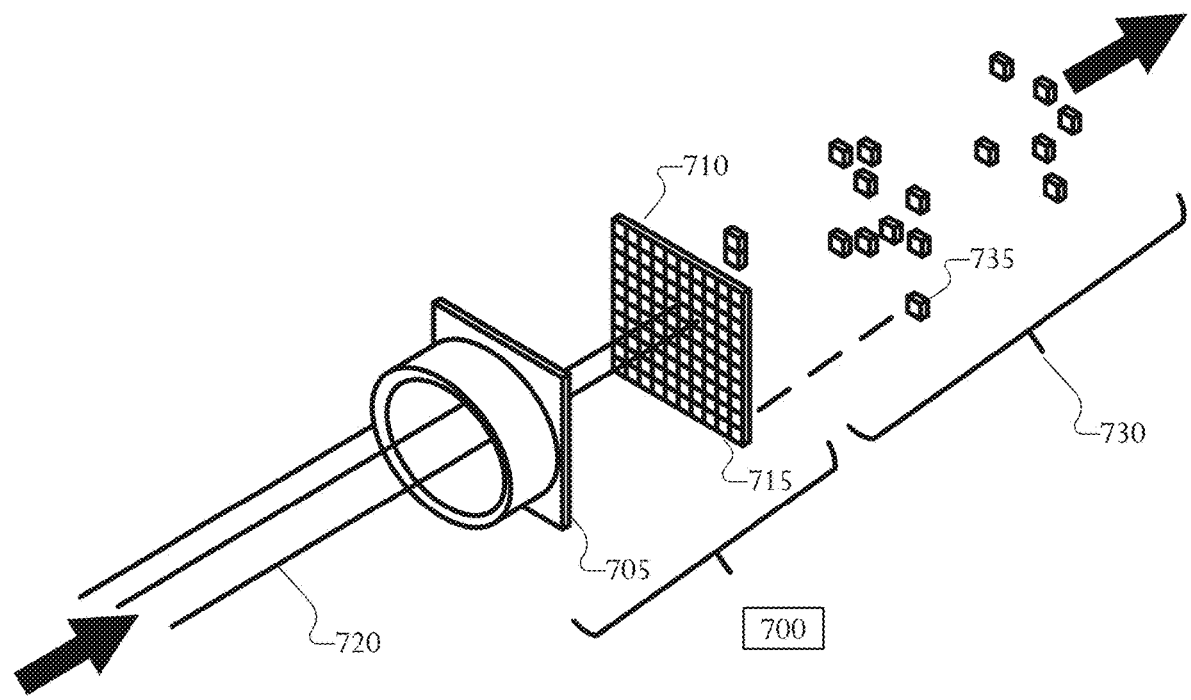
FIG. 7A illustrates aspects of the operation of a DVS camera according to embodiments of the present disclosure.

FIG. 7A illustrates aspects of the operation of a dynamic vision sensor ("DVS") camera 700 according to embodiments of the present disclosure. The embodiment shown in FIG. 7A is for illustration only and other embodiments could be used without departing from the scope of the present disclosure. The DVS camera 700 can be configured the same as, or similar to, DVS camera 505 and can include one or more processors and sensors configured to capture one or more images as illustrated herein.

According to various embodiments, DVS camera 700 includes a lens assembly 705, and a pixelated array 710 of light intensity sensors, such as light intensity sensor 715. In some embodiments, lens assembly 705 comprises an optical lens having a focal length corresponding to a distance between lens assemble 705 and pixelated array 710. In various embodiments according to this disclosure, the lens assembly 705 includes an aperture for adjusting (such as by stepping down an f-stop) the overall intensity of light provided to pixelated array 710.

As shown in the non-limiting example of FIG. 7A, the pixelated array 710 of light intensity sensors includes an array of light intensity sensors (for example, light intensity sensor 715) substantially covering an area in the focal plane of a lens in lens assembly 705. Further, the output each light intensity sensor of pixelated array 710 is mapped to a spatial coordinate value.

In some embodiments, the light intensity sensor 715 includes a photo sensor configured to output a signal corresponding to a direction of change in the measured intensity of light received at light intensity sensor 715. According to certain embodiments, the output of light intensity sensor is a binary signal, for example "1" for an increase in the measured intensity of light, and "0" for a decrease in the measured intensity of light. When there is no change in the measured intensity of light at light intensity sensor 715, no signal is output. According to certain embodiments, signals output by light intensity sensor 715 are time-coded or time-mapped to a time value by pixelated array 710 or by another downstream component or module (such as eye tracking processor/component/module 1010 in FIG. 10 herein below).

Referring to the non-limiting example of FIG. 7A, at a high level, the DVS camera 700 operates by receiving light 720 through lens assembly 705, and converting the received light into one or more time coded event streams 730, by using the output of the constituent light intensity sensors of pixelated array 710. Each pixel sensor works asynchronously. Each pixel includes a different timestamp. The timestamp corresponds of the time when the pixel sensor detects a change in intensity (based on a threshold). Only local pixel changes are transmitted, at the time a respective pixel change occurs.

Figure 7B:
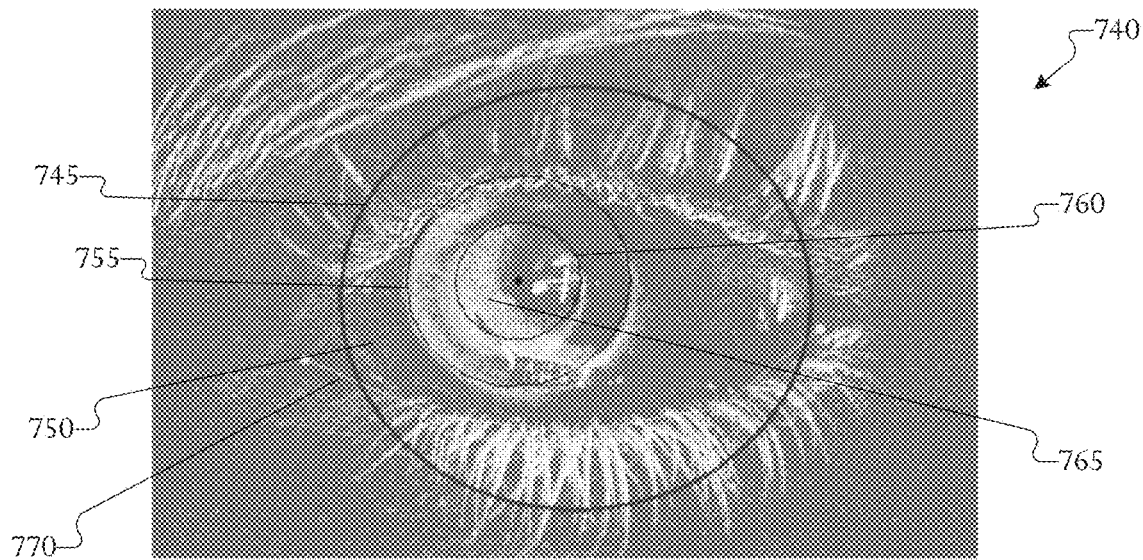
FIG. 7B illustrates a 640×480 buffer of DVS pixels during a 10 ms period of time according to embodiments of the present disclosure.
Figure 9:
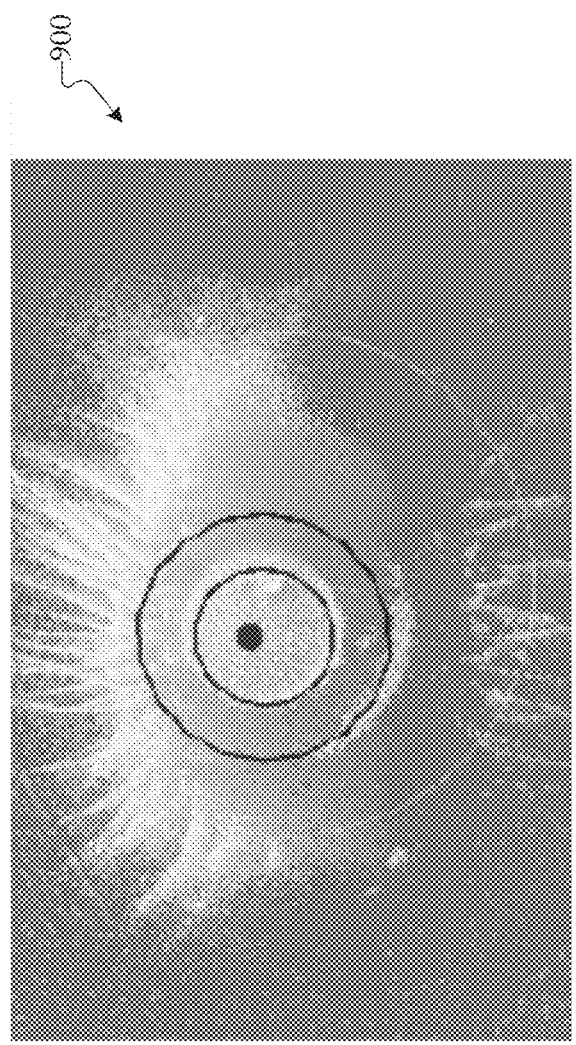
FIG. 9 illustrates a 640×480 buffer of DVS pixels during a 10 ms period of time, representing a blink according to embodiments of the present disclosure.

According to various embodiments, the event stream 730 includes a time-coded stream of light intensity change events output by light intensity sensors of pixelated array 710. An individual light intensity change event 735 includes data indicating a change (for example, an increase or decrease) in the measured intensity of the light measured at a particular light intensity sensor (e.g., a pixel) of pixelated array 710. For example, in this illustrative example, light intensity change event 735 corresponds to a change in the measured light intensity at light intensity sensor 715. Further, each individual light intensity change event 735 is time-coded and asynchronous. In certain embodiments, pixels are stored in a buffer (for example for blink detection), namely not in the sensor itself, thereafter. In some embodiments, each individual light intensity change event 735 is also mapped to a value in a spatial coordinate system (for example, a coordinate system based on the rows and columns of pixelated array 710). In certain embodiments, the pixelated array 710 is a FYI pixel array that corresponds to the resolution of the sensor, such as 640×480. The mapped individual light intensity change events can be buffered, or gathered, over a specified period of time (for example 10 milliseconds (ms)) to generate a DVS image (for example, a DVS image frame) 740 as shown in FIG. 7B. In certain embodiments, the DVS-pixels on for blink detection are only gathered and for display (i.e., debugging) as shown in FIGS. 7B and 9 (below). In such embodiments the DVS-pixel in a buffer are not gathered for tracking. In certain embodiments, this operation is performed after receiving asynchronous DVS-pixel from the sensor.

FIG. 7B illustrates a DVS image 740 according to embodiments of the present disclosure. The embodiment of the DVS image shown in FIG. 7B is for illustration only and other embodiments could be used without departing from the scope of the present disclosure.

Referring to the non-limiting example in FIG. 7B, the DVS camera 700 is configured to focus on, or otherwise capture, a region 745 around an eye 750 of the wearer. Additionally, the DVS camera 700 can identify certain landmark features of the eye, such as an eye lid 770, an iris 755 and a pupil 760. Each individual light intensity change event 735 that is captured over a period of time appears white 765 against a dark background of DVS image 740. That is, as the iris 755 and pupil 760 move (such as compared to a previous or buffer image of the eye), the white 765 appears on the DVS image 740.

Figure 8A:
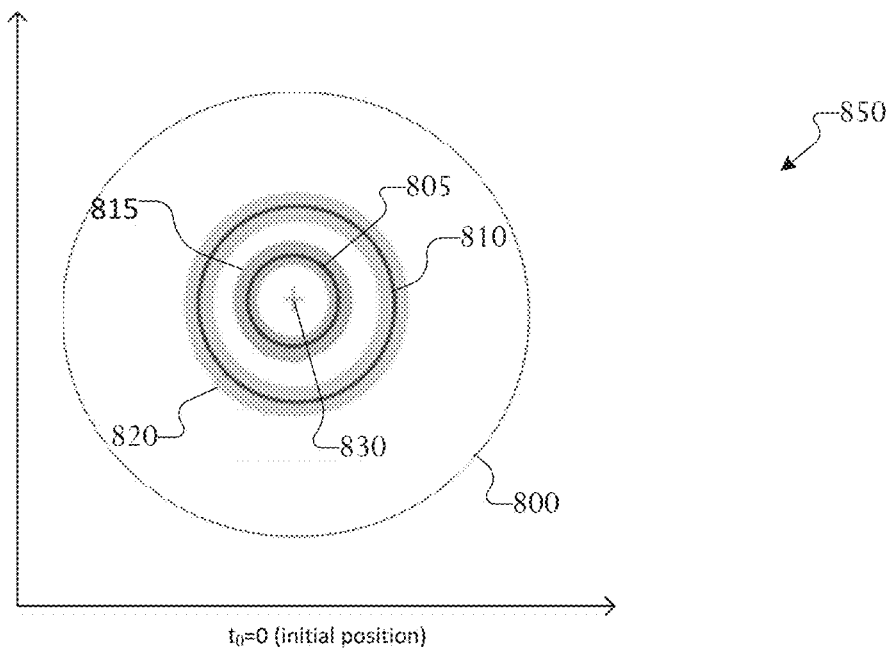
FIGS. 8A and 8B illustrate an example of cluster-based shifting enabled by one or more DVS cameras according to embodiments of the present disclosure.
Figure 8B:
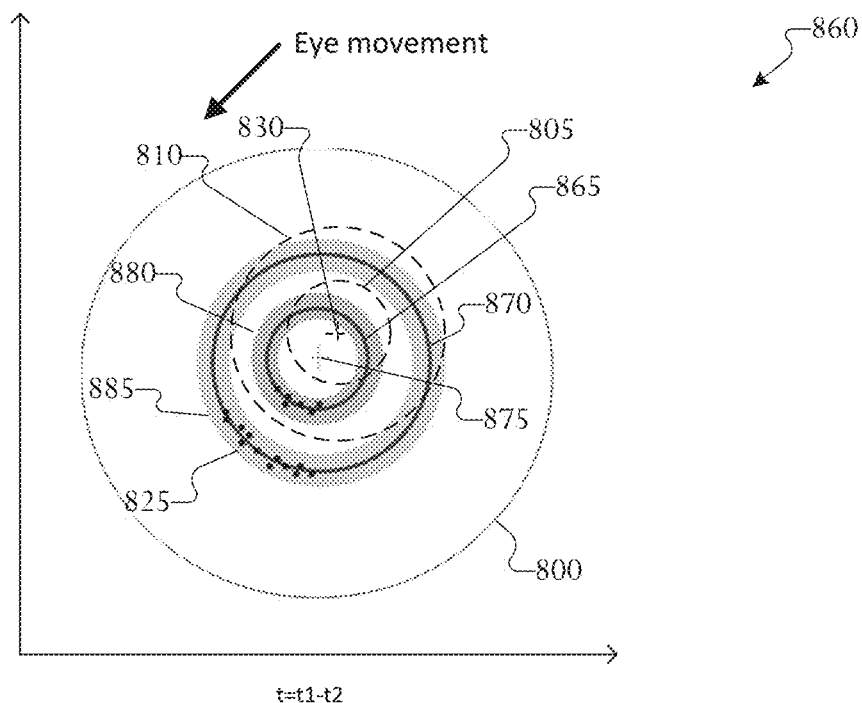

FIGS. 8A and 8B illustrate an example of a cluster-based shifting process enabled by one or more DVS cameras according to embodiments of the present disclosure. The embodiment shown in FIGS. 8A and 8B are for illustration only and other embodiments could be used without departing from the scope of the present disclosure. According to embodiments of the present disclosure, the cluster-based shifting process is repeated continuously by an eye tracking component, module, or processor (for example, hardware component for performing eye tracking, software module/process for performing eye tracking, or a combination thereof), such as eye tracking processor 1010 of FIG. 10, during AR (or VR) experiences.

FIG. 8A illustrates an example of an initial mapping 850 of a user eye 800. The initial mapping 850 include a pupil ellipse 805 and an iris ellipse 810. In certain embodiments, an eye tracking processor (for example, software, hardware, or a combination thereof), such as eye tracker processor 1010, performs an initialization process and creates the initial mapping 850 of user eye 800 based on an CMOS image captured by an CMOS camera at an initial time of $t_0$. For example, the object detection/recognition technology can be utilized with respect to the CMOS image to determine the circumferences/edges of the pupil and the iris, and thus respectively determine the pupil ellipse 805 and the iris ellipse 810. In other embodiments, the eye tracking processor (for example, hardware and/or software), such as eye tracker processor 1010, creates the initial mapping 850 of user eye 800 based on the DVS image 740 captured by DVS 700 camera at the initial time of $t_0$. For example, object detection/recognition technology can be utilized with respect to the DVS image to determine the circumferences/edges of the pupil and the iris, and thus respectively determine the pupil ellipse 805 and the iris ellipse 810. The initial mapping 850 also includes a pupil cluster 815 and an iris cluster 820. In some implementations, the clusters can be generated by the eye tracking processor based on the respective ellipses. The pupil cluster 815 comprises a predefined boundary around pupil ellipse 805. Similarly, an iris cluster 820 comprises a predefined boundary around iris ellipse 810. In certain embodiments, the clusters corresponding to pupil ellipse 805 and iris ellipse 810 have a thickness of (±8 pixels). An eye center 830 of user eye 800 is calculated based on the concentric pupil ellipse 805 and iris ellipse 810 for the initial mapping 850.

FIG. 8B illustrates an example of a second, or subsequent, mapping 860 of user eye 800 showing the shifting of the ellipses and eye center based on at least one DVS-on pixel 825 (i.e. light intensity change events 635 from FIG. 7A). The second (or subsequent) mapping 860 illustrates a mapping of the eye captured at a time tn after the initial mapping 850. A DVS-pixel is on if it detects a change in intensity in the scene (based on a threshold). If the at least one DVS-on pixel 825 falls within the pupil cluster 815 or iris cluster 820 the eye tracking processor 1010 shifts the positions of the pupil ellipse 805 and/or iris ellipse 810 toward the DVS-on pixel. Consequently, the pupil cluster 815, iris cluster 820, and eye center 830 shift as well. The eye tracking processor 1010 performs this operation for each DVS pixel-on (or DVS-on pixel), at a very high rate. As such, the eye position is always moving. That is, at time tn, after initial mapping 850 of user eye 800 is generated, the eye tracking processor, such as eye tracking processor 1010, creates the second mapping 860 of user eye 800. The eye tracking processor generates the second mapping 860 based on a plurality of DVS-on (i.e. DVS-triggered, DVS-fired, DVS-event, light intensity change event, etc.) pixels 825 and the initial mapping 850. The DVS-on pixels 825 are created when each individual light intensity change event 635 is gathered over a period of time, $t_1$-$t_2$, (for example 10 ms). After the DVS-on pixels 825 that occur in the pupil cluster 815 and the iris cluster 820 are processed, the eye tracking processor shifts (identifies and shifts) a second pupil ellipse 865, a second iris ellipse 870, and a second eye center 885. The eye tracking processor calculates a direction of the eye movement based on a change, namely a delta, between the eye center 830 and the second eye center 875 in the spatial coordinate system. The eye tracking processor also shifts (identifies and shifts) a second pupil cluster 880 in the second mapping 860. The second pupil cluster 880 is a predefined boundary around second pupil ellipse 865. Similarly, the eye tracking processor determines second iris cluster 885 which is a predefined boundary around iris ellipse 870. In certain embodiments, the eye tracking processor repeats the cluster-based tracking continuously while the electronic device, namely the HMD or wearable device, is in use.

FIG. 9 illustrates an image of a blink 900 captured by a DVS camera according to embodiments of the present disclosure. The example of the blink 900 shown in FIG. 9 is for illustration only and other illustrations could be used without departing from the scope of the present disclosure.

In certain embodiments, an electronic device, such as an HMD 500 or wearable device 520, can detect a blink 900. A blink detection module, component, or processor 1015 gathers DVS-on pixels 825 in a buffer. When the number of DVS-on pixels 825 inside the user eye 800 is greater than a specified threshold for a fixed period of time, such as for example, 1 ms, a blink 900 is detected. In the example shown in FIG. 9, the DVS-on pixels 825 are depicted as white portions of the image. If the blink 900 is detected, a blink detection module, component, or processor 1015 (for example, hardware and/or software) in the electronic device sends instructions to an eye tracking processor in the electronic device to freeze tracking during a duration of the blink 900.

Figure 10:
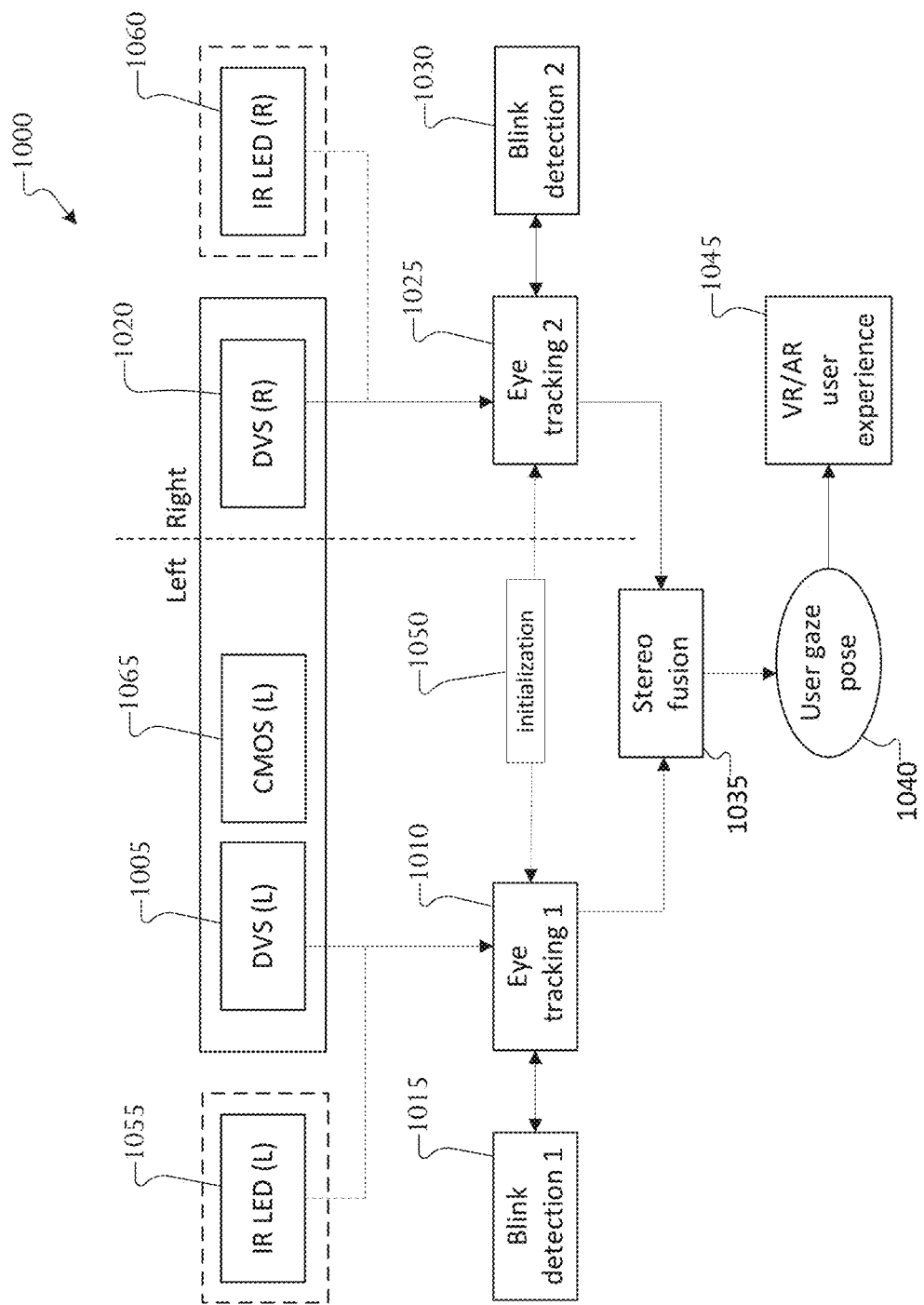
FIG. 10 is a block diagram that illustrates gaze tracking circuitry of the hybrid eye tracker using a set of two DVS cameras and one CMOS camera with optional Infrared LEDs according to embodiments of the present disclosure.

FIG. 10 illustrates an electronic device 1000 having gaze tracking circuitry according to embodiments of the present disclosure. The embodiment of the electronic device shown in FIG. 10 is for illustration only and other examples could be used without departing from the scope of the present disclosure. The electronic device 1000 can be configured as the HMD 400, HMD 500, or wearable device 520, and can be the same as, or similar, to one of the electronic devices 101, 102, 104, 210 or 220.

According to certain embodiments, the electronic device 1000 includes at least one DVS camera 1005, an eye tracking processor 1010 and a blink detection processor 1015. The eye tracking processor 1010 is configured to detect the position of an eye of the user by using the output generated by the DVS camera 1005 to track eye movement using cluster-based shifting (as described above and shown in FIGS. 8A & 8B). The blink detection processor 1015 is coupled to eye tracking processor 1010 to assist in tracking the eye movement. The blink detection processor 1015 is able to detect a blink 900 when the number of each light intensity change event 635 inside the user eye 800 is greater than a specified threshold for a fixed period of time, such as for example, 1 ms. When the blink detection processor 1015 detects a blink, the blink detection processor 1015 generates and transmits a signal to the eye tracking processor 1010 to pause tracking of the eye for a specified duration (period) of time (as disclosed in FIG. 9B above).

In certain embodiments, the electronic device 1000 includes a second DVS camera 1020, a second eye tracking processor 1025, and a second blink detection processor 1030. The second DVS camera 1020, second tracking processor 1025, and second blink detection processor 1030 can perform eye tracking and blink detection on a second eye of the wearer. In certain embodiments, the electronic device 1000 includes a stereo fusion processor (or component or module) 1035 coupled to one or both of the eye tracking processor 1010 or the second eye tracking processor 1025 to determine a user eye pose 1040, such as for use in an AR (or VR) application 1045. The stereo fusion processor 1035 gathers eye centers, ellipses, and/or elliptical clusters from one or both of the eye tracking processor 1010 or the second eye tracking processor 1025. The stereo fusion processor 1035 merges two eye poses (for example, one eye pose from each eye) to determine and provide the user gaze pose 1040, such as for the AR (or VR) application 1045. The stereo fusion processor 1035 utilizes any appropriate algorithm for merging the eye poses In certain embodiments, the electronic device 1000 includes one or more illumination sources 1055, 1060 coupled to the DVS camera 1005, or second DVS camera 1020, or both. The illumination sources 1055, 1060 can be any suitable source of light, such as an Infrared Light Emitting Diode (IR LED). In certain embodiments, the electronic device 1000 includes circuitry to implement an initialization process 1050 utilizing one or CMOS cameras 1065, and one or more illumination sources 1055, 1060.

Figure 11:
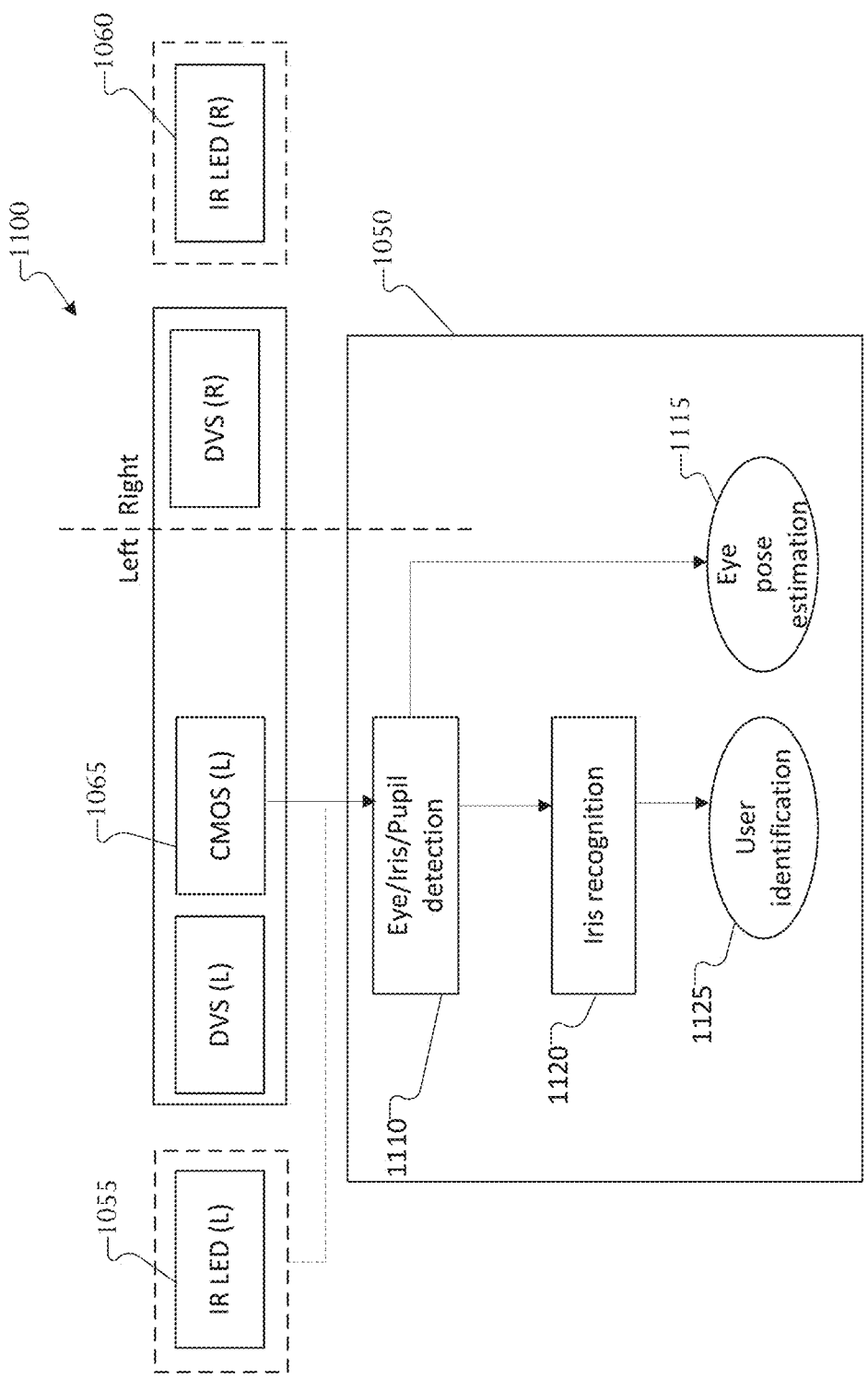
FIG. 11 is a block diagram that illustrate an initialization process to be performed by the hybrid eye tracker on one of the two eyes, using one DVS camera and one CMOS camera according to embodiments of the present disclosure.

FIG. 11 illustrates an electronic device 1100 having additional circuitry for user identification 1125 and eye pose estimation 1115, such as during initialization 1050, according to embodiments of the present disclosure. The embodiment of the electronic device 1100 shown in FIG. 11 is for explanation only and other illustrations could be used without departing from the scope of the present disclosure. The electronic device 1100 can be configured as the HMD 400, HMD 500, or wearable device 520, and can be the same as, or similar to, one of the electronic devices 101, 102, 104, 210, 220, or 1000.

In certain embodiments, the electronic device 1100 includes a CMOS camera 1065. The CMOS camera 1065 is a digital camera comprising a lens for receiving light and a pixelated sensor upon which the received light is focused. According to various embodiments, the complementary metal-oxide semiconductor (CMOS) camera 1065 is a red-green-blue (RBG) camera, which periodically outputs frames of raw received light data from each pixel of its pixelated sensor. In certain embodiments, the CMOS camera 1065 can be used in conjunction with one or more illumination sources 1055, 1060. The output of CMOS camera 1065 is communicated (i.e., transmitted, sent or provided) to an eye/iris/pupil detection processor (or component or module) 1110. The eye/iris/pupil detection processor 1110 (for example, software and/or hardware) is adapted to assist with initial mapping 850 of user eye 800 and creates an eye pose estimation 1115. The eye pose estimation 1115 is communicated to eye tracking processor 1010 and second eye tracking processor 1025. The eye tracking processor 1010 and second eye tracking processor 1025 use the eye pose estimation 1115 to create initial mapping 850 of each user eye 800. According to embodiments of the present disclosure, the CMOS camera 1065 is turned off (i.e., powered-off) after initialization 1050 is complete. According to embodiments of the present disclosure, initialization 1050 occurs in a manner similar to that when only DVS camera 1005 and eye tracking processor 1010 are present.

In certain embodiments, electronic device 1000 includes CMOS camera 1065 coupled to an eye/iris/pupil detection processor 1110. The eye/iris/pupil detection processor 1110 is further coupled to an iris recognition processor (or component or module) 1120. Iris recognition processor 1120 can be configured to identify a user 1125. For example, the iris recognition processor 1120 can analyze data from the CMOS camera 1065 to identify the wearer based on iris recognition.

Figure 12:
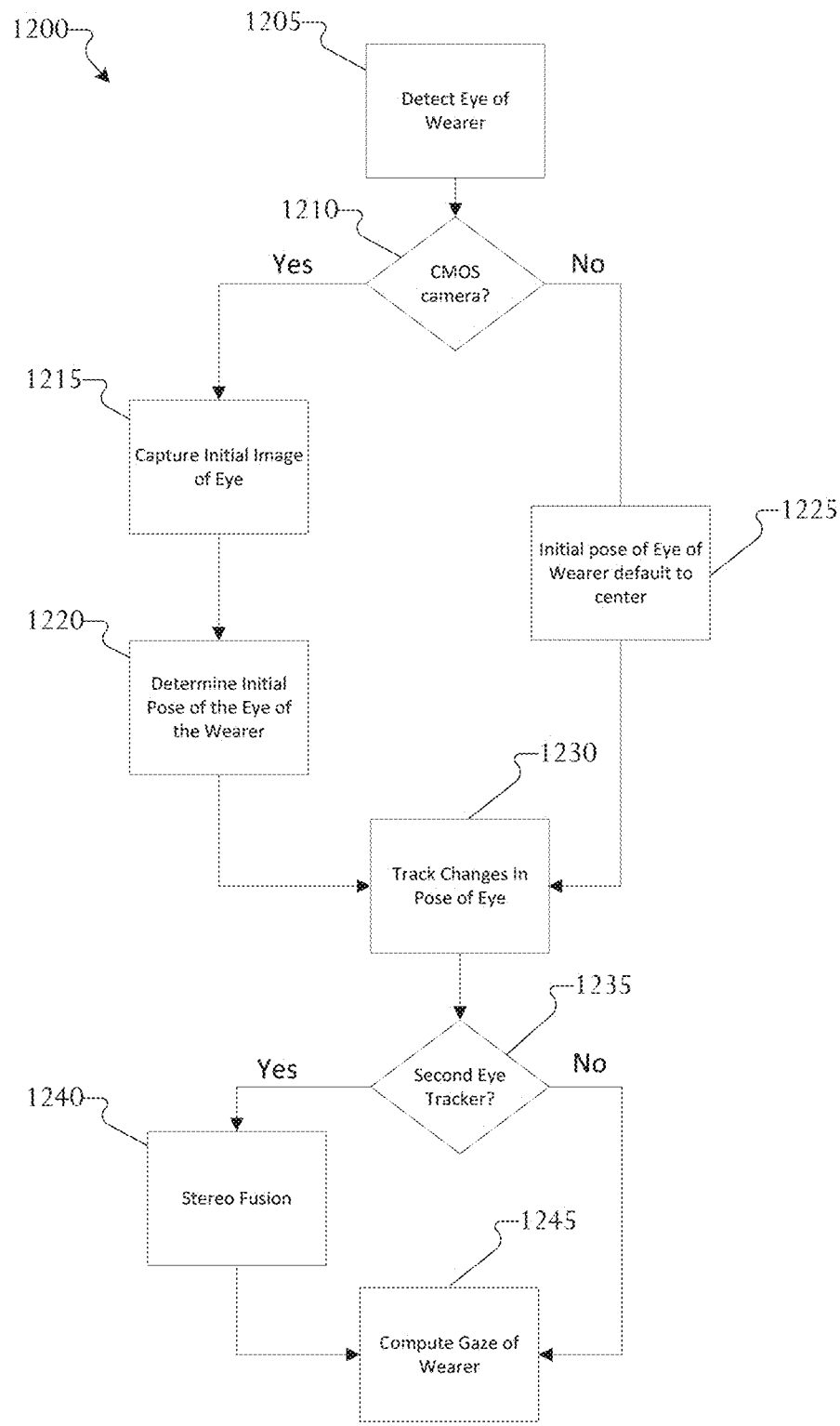
FIG. 12 illustrates a process for gaze tracking according to embodiments of the present disclosure.

FIG. 12 illustrates a process for gaze tracking according to embodiments of the present disclosure. While the flow chart depicts a series of sequential steps, unless explicitly stated, no inference should be drawn from that sequence regarding specific order of performance, performance of steps or portions thereof serially rather than concurrently or in an overlapping manner, or performance of the steps depicted exclusively without the occurrence of intervening or intermediate steps. The process depicted in the example depicted is implemented by a processor in, for example, a head mounted electronic device or a wearable electronic device.

In block 1205, the electronic device detects at least one eye of a wearer of the electronic device. For example, the electronic device can be configured as HMD 400, HMD 500, or wearable device 520. In certain embodiments, the electronic device includes one or more cameras, such as a DVS camera 510, a CMOS camera 505, or a combination thereof. In some embodiments, object detection or recognition technology can be utilized, based on pixel information received from the one or more cameras, to detect or recognize the at least one eye of the wearer.

In block 1210, if the camera is, or includes, CMOS camera 505, the camera captures an initial image of the eye of the wearer in block 1215. For example, the camera can "see" or be directed toward the eye and transmit, to one or more processors in the electronic device, a signal comprising information, such as a plurality of pixels, regarding the eye. In certain embodiments, the CMOS camera 505 can capture an image of the eye and transmit data associated with the eye to one or more processors in the electronic device. The one or more processors, which can include eye tracking processor/component/module 1010 or blink detection processor/component/module 1015, identify features within the eye.

In block 1220, the one or more processors determine an initial pose of the eye of the wearer based on the information regarding the eye received from CMOS camera 505 in block 1215. For example, the one or more processors can determine the initial pose of the eye based on the image captured.

If the camera does not include CMOS camera 505 in block 1210, the one or more processors sets an initial pose of the eye of the wearer to the center as a default. For example, when only one or more DVS cameras are present, an initial pose of the eye of the wearer defaults to center in block 1225.

In block 1230, changes in the pose of the eye are tracked. For example, one or both of the eye tracking processor 1010 or the second eye tracking processor 1025 gather eye centers, ellipses, and/or elliptical clusters to calculate, determine, or identify changes in the pose of the eye of the wearer. In some embodiments, one or more processors receive a stream of DVS-on pixel data from the DVS camera 510 and track the one or more changes to the initial pose of the eye of the wearer. In some cases, such as when power (for example, battery life), robustness (for example, dynamic range, motion blur), or other factors are less of a concern, the CMOS camera 505 can be also utilized to facilitate tracking or determining eye pose change.

If the electronic device includes a second eye tracking capability in block 1235, stereo fusion may be performed using the second eye tracker. For example, if the second eye tracker is present, the electronic device performs stereo fusion in block 1240, The stereo fusion processor 1035 merges two eye poses (for example, one eye pose from each eye) to determine and provide the user gaze pose 1040 to an AR (or VR or XR) application 1045. The stereo fusion processor 1035 utilizes any appropriate algorithm for merging the eye poses. Thereafter, the process proceeds to block 1245 to compute the gaze of the wearer. If the electronic device does not include a second eye tracker in block 1235, the process proceeds to block 1245 to compute the gaze of the wearer.

In block 1245, the user gaze pose 1040 is computed based on stereo fusion for two eyes or on single eye pose information. While the stereo fusion processor improves the accuracy of the user gaze pose estimation, in some embodiments the stereo fusion processor is optional. In some cases, user gaze pose estimation can be based on a single eye pose from a single eye since a user's eyes generally look at the same direction.

The DVS camera 510 continuously transmits data associated with the eye to one or more processors in the electronic device. The tracker is using data stream coming from the DVS sensor directly. In certain embodiments, the data stream is gathered into a buffer only for blink detection. In certain embodiments, the system does not display DVS images (a DVS image can be generated from a DVS pixel data stream for a duration of time), but can use DVS images for debugging. The one or more processors, such as eye tracking processor 1010 or blink detection processor 1015, identify features within the continuous stream (subsequent to the initial) of pixels-on events of the eye.

Although various features have been shown in the figures and described above, various changes may be made to the figures. For example, the size, shape, arrangement, and layout of components shown in FIGS. 1 through 10, are for illustration only. Each component could have any suitable size, shape, and dimensions, and multiple components could have any suitable arrangement and layout. Also, various components in FIGS. 1 through 11 could be combined, further subdivided, or omitted and additional components could be added according to particular needs. Further, each component in a device or system could be implemented using any suitable structure(s) for performing the described function(s). In addition, whiles FIG. 12 illustrates various series of steps, various steps in FIG. 12 could overlap, occur in parallel, occur multiple times, or occur in a different order.

None of the description in this application should be read as implying that any particular element, step, or function is an essential element that must be included in the claim scope. The scope of patented subject matter is defined only by the claims. Moreover, none of the claims is intended to invoke 35 U.S.C. § 112(f) unless the exact words "means for" are followed by a participle.

What is claimed is:

1. An electronic device comprising:
   at least two cameras configured to capture pixel changes from of an eye of a wearer of the electronic device, the at least two cameras comprising at least one Dynamic Vision Sensor (DVS) camera and at least one complementary metal-oxide sensor (CMOS) camera; and
   one or more processors configured to:
      receive, from the at least one CMOS camera, information associated with the eye,
      initialize an initial pose of the eye based on the information,
      receive DVS pixel data from the at least one DVS camera,
      track one or more changes to the initial pose of the eye based on the DVS pixel data, and
      based on the one or more changes to the initial pose of the eye, determine a gaze of the wearer.

2. The electronic device of claim 1, wherein to track the one or more changes to the initial pose of the eye, the processor is further configured to:

determine, based on the initial pose, a pupil ellipse and a pupil cluster;

determine, based on the initial pose, an iris ellipse and an iris cluster;

determine, based on at least one of the pupil ellipse or the iris ellipse, an eye center;

detect, based on the DVS pixel data, one or more DVS-on pixels within at least one of the pupil cluster or the iris cluster;

determine a subsequent pupil ellipse and a subsequent pupil cluster corresponding with the DVS-on pixels;

determine a subsequent iris ellipse and a subsequent iris cluster corresponding with the DVS-on pixels;

determine, based on at least one of the subsequent pupil ellipse or the subsequent iris ellipse, a subsequent eye center;

determine a subsequent pose of the eye based on at least one of the subsequent pupil ellipse, the subsequent iris ellipse, or the subsequent eye center; and track eye movement based on a change from the initial pose of the eye to the subsequent pose of the eye.

3. The electronic device of claim 1, wherein the processor is further configured to:

detect, based on the DVS pixel data, a blink associated with the eye of the wearer; and cease, during a time period of the blink, tracking the one or more changes to the initial pose of the eye.

4. The electronic device of claim 1, wherein the one or more cameras includes at least two DVS cameras, wherein the DVS pixel data comprises stereo DVS pixel data associated with the eye of the wearer and a second eye of the wearer, and wherein the processor is configured to:

perform stereo fusion based on the stereo DVS pixel data received from the at least two DVS cameras to align the center of the eye and a second center associated with the second eye; and determine the gaze of the wearer based on stereo fusion.

5. The electronic device of claim 1, wherein the processor is configured to vary an operation of at least one of an application or an external device as a function of the gaze of the wearer.

6. The electronic device of claim 1 wherein the processor is further configured to identify the wearer based on iris recognition performed with respect to an image generated from CMOS image data.

7. The electronic device of claim 1, further comprising one or more illumination sources coupled to the one or more cameras.

8. The electronic device of claim 1 wherein the processor causes the at least one CMOS camera to power off subsequent to the initial pose being determined.

9. The electronic device of claim 1, wherein the electronic device includes at least one of: a wearable device, a Head Mounted Display (HMD) or headset, or an add-on component operable with the wearable device of the HMD or headset.

10. The electronic device of claim 1, wherein the processor is configured to initialize the initial pose of the eye by recording a plurality of landmarks of the eye of the wearer.

11. A method comprising:

capturing, by one or more cameras, pixel changes from an eye of a wearer of an electronic device, the one or more cameras comprising at least one Dynamic Vision Sensor (DVS) camera;

receiving, from at least one CMOS camera, information associated with the eye, initializing an initial pose of the eye based on the information;

receiving DVS pixel data from the at least one DVS camera, tracking one or more changes to the initial pose of the eye based on the DVS pixel data; and determining a gaze of the wearer based on the one or more changes to the initial pose of the eye.

12. The method of claim 11, wherein tracking changes in the pose of the eye further comprises:

determining, based on the initial pose, a pupil ellipse and a pupil cluster;

determining, based on the initial pose, an iris ellipse and an iris cluster;

determining, based on at least one of the pupil ellipse or the iris ellipse, an eye center;

detecting, based on the DVS pixel data, one or more DVS-on pixels within at least one of the pupil cluster or the iris cluster;

determining a subsequent pupil ellipse and a subsequent pupil cluster corresponding with the DVS-on pixels;

determining a subsequent iris ellipse and a subsequent iris cluster corresponding with the DVS-on pixels;

determining, based on at least one of the subsequent pupil ellipse or the subsequent iris ellipse, a subsequent eye center;

determining a subsequent pose of the eye based on at least one of the subsequent pupil ellipse, the subsequent iris ellipse, or the subsequent eye; and tracking eye movement based on the change from the initial pose of the eye to the subsequent pose.

13. The method of claim 11, further comprising:

detecting, based on the DVS pixel data, a blink associated with the eye of the wearer; and ceasing, during a time period of the blink, tracking the one or more changes to the initial pose of the eye.

14. The method of claim 11, further comprising identifying the wearer based on an initial image of the eye.

15. A non-transitory computer readable medium configured to store a plurality of instructions that, when executed by at least one processor, are configured to cause the at least one processor to:

receive, from one or more cameras, pixel changes from of an eye of a wearer of an electronic device, the one or more cameras comprising at least one DVS camera, receive, from at least one CMOS camera, information associated with the eye;

initialize an initial pose of the eye based on the information;

receive DVS pixel data from the at least one DVS camera;

track one or more changes to the initial pose of the eye based on the DVS pixel data; and determine a gaze of the wearer based on the one or more changes to the initial pose of the eye.

16. The non-transitory computer readable medium of claim 15, wherein the plurality of instructions is further configured to cause the at least one processor to:

determine, based on the initial pose, a pupil ellipse and a pupil cluster;

determine, based on the initial pose, an iris ellipse and an iris cluster;

determine, based on at least one of the pupil ellipse or the iris ellipse, an eye center;

detect, based on the DVS pixel data, one or more DVS-on pixels within at least one of the pupil cluster or the iris cluster;

determine a subsequent pupil ellipse and a subsequent pupil cluster corresponding with the DVS-on pixels;

determine a subsequent iris ellipse and a subsequent iris cluster corresponding with the DVS-on pixels;

determine, based on at least one of the subsequent pupil ellipse or the subsequent iris ellipse, a subsequent eye center;

determine a subsequent pose of the eye based on at least one of the subsequent pupil ellipse, the subsequent iris ellipse, or the subsequent eye center; and track eye movement based on the change from the initial pose of the eye to the subsequent pose of the eye.

17. The non-transitory computer readable medium of claim 15, wherein the plurality of instructions is further configured to cause the at least one processor to:

detect, based on the DVS pixel data, a blink associated with the eye of the wearer; and cease, during a time period of the blink, tracking the one or more changes to the initial pose of the eye.

18. The non-transitory computer readable medium of claim 15, wherein the plurality of instructions is further configured to cause the at least one processor to:

perform stereo fusion based on stereo DVS pixel data received from a stereo pair of DVS cameras to align the center of the eye and a second center associated with a second eye of the wearer; and determine the gaze of the wearer based on the stereo fusion.

19. The non-transitory computer readable medium of claim 15, wherein the plurality of instructions is further configured to cause the at least one processor to identify the wearer based on iris recognition performed with respect to an image generated from CMOS data.

20. The non-transitory computer readable medium of claim 15, wherein the plurality of instructions is further configured to cause the at least one processor to initialize the initial pose of the eye by recording a plurality of landmarks of the eye of the wearer.

\* \* \* \* \*